United States Patent
Mechetner et al.

(10) Patent No.: US 7,144,704 B2
(45) Date of Patent: *Dec. 5, 2006

(54) METHODS AND REAGENTS FOR PREPARING AND USING IMMUNOLOGICAL AGENTS SPECIFIC FOR P-GLYCOPROTEIN

(75) Inventors: Eugene Mechetner, Irvine, CA (US); John Fruehauf, Tustin, CA (US)

(73) Assignee: Oncotech, Inc., Irvine, CA (US)

(*) Notice: Subject to any disclaimer, the term of this patent is extended or adjusted under 35 U.S.C. 154(b) by 664 days.

This patent is subject to a terminal disclaimer.

(21) Appl. No.: 10/114,847

(22) Filed: Apr. 2, 2002

(65) Prior Publication Data

US 2006/0211051 A1    Sep. 21, 2006

Related U.S. Application Data

(60) Division of application No. 09/316,167, filed on May 21, 1999, now Pat. No. 6,365,357, which is a continuation-in-part of application No. 08/752,447, filed on Nov. 15, 1996, now Pat. No. 5,994,088.

(51) Int. Cl.
G01N 33/53 (2006.01)
G01N 33/567 (2006.01)
G01N 33/574 (2006.01)
C12Q 1/00 (2006.01)
C07K 1/00 (2006.01)
C07K 14/00 (2006.01)

(52) U.S. Cl. ............ 435/7.1; 435/4; 435/7.21; 435/7.2; 435/7.23; 530/350; 530/387.1; 530/387.7; 436/86; 436/87; 436/164; 436/536

(58) Field of Classification Search .......... 435/4, 435/7.1, 7.21, 7.23; 530/350, 387.1, 387.7; 436/164, 86, 87, 536

See application file for complete search history.

(56) References Cited

U.S. PATENT DOCUMENTS

| | | |
|---|---|---|
| 4,837,306 A | 6/1989 | Ling et al. |
| 4,918,163 A | 4/1990 | Young et al. |
| 4,925,787 A | 5/1990 | Tanihara et al. |
| 5,057,598 A | 10/1991 | Pollack et al. |
| 5,061,620 A | 10/1991 | Tsukamoto et al. |
| 5,091,513 A | 2/1992 | Huston et al. |
| 5,130,127 A | 7/1992 | Herlyn |
| 5,132,405 A | 7/1992 | Huston et al. |
| 5,134,075 A | 7/1992 | Hellstrom et al. |
| 5,204,095 A | 4/1993 | Goodall et al. |
| 5,206,352 A | 4/1993 | Roninson et al. |
| 5,215,913 A | 6/1993 | Posner |
| 5,434,075 A | 7/1995 | Mechetner et al. |
| 5,464,753 A | 11/1995 | Chaudhary et al. |

FOREIGN PATENT DOCUMENTS

WO    WO 93 19094 A1    9/1993

OTHER PUBLICATIONS

Akiyama et al., "Most Drugs that Reverse Multidrug Resistance Also Inhibit Photoaffinity Labeling of P-Glycoprotein by a vinblastine Analog", *Molec. Pharm.* 33:144(1988).
Arcesi et al., "Monoclonal Antibody to an External Epitope of the Human mdr1 P-Glycoprotein[1]" *Cancer Res.* 53:310-317(1993).
Ball et al., "Correlation of CD34 and Multi-Drug Resistance P170 with FAB and Cytogenetics but not prognosis in Acute Myeloid Leukemia", 1990 *Blood* 76(10, Suppl 1):252a.
Barth et al., "Interferon γ and Tumor Necrosis Factor Have a Role in Tumor Regressions Mediated by Murine CD8+ Tumor-infiltrating Lymphocytes", 1991, *J. Exp. Med.* 173:647-658.
Beck et al., "Do Anti-P-Glycoprotein Antibodies Have a Future in the Circumvention of Multidrug Resistance", *J. Natl. Cancer Inst.* 83:1364-1366, Oct. 2, 1991.
Chaudhary et al., "Expression and Activity of P-Glycoprotein, a Multidrug Efflux Pump, in Human Hematopoietic Stem Cells" *Cell* 66:85 (1991).
Chaudhary et al., "Expression and Activity of the Multidrug Resistance P-Glycoprotein in Human Peripheral Blood Lymphocytes", *Blood* 80:2735 (1992).
Chen et al., "Internal Duplication and Homology with Bacterial Transport Proteins in the mdr1 (P-Glycoprotein) Gene from Multidrug-Resistant Human Cells" *Cell* 47:381 (1986).
Choi et al., An Altered Pattern of Cross-Resistance Human Cells Results from Spontaneous Mutations in the mdr 1 (P-Glycoprotein) Gene *Cell* 53:519-529 (1988).
Choi et al., "Multidrug resistance after retroviral transfer of the human MDR1 gene correlates with P-Glycoprotein density in the plasma membrane and is not affected by cytotoxic selection", *Proc. Natl. Acad. Sci. USA* 88:7386-7390 (1991).

(Continued)

Primary Examiner—Alana M. Harris
(74) Attorney, Agent, or Firm—McDonell Boehnen Hulbert & Berghoff

(57) ABSTRACT

This invention relates to immunological reagents and methods specific for a mammalian, transmembrane protein termed Pgp, having a non-specific efflux pump activity established in the art as being a component of clinically-important multidrug resistance in cancer patients undergoing chemotherapy. The invention provides methods for developing and using immunological reagents specific for certain mutant forms of Pgp and for wild-type Pgp in a conformation associated with substrate binding or in the presence of ATP depleting agents. The invention also provides improved methods for identifying and characterizing anticancer compounds.

6 Claims, 35 Drawing Sheets

OTHER PUBLICATIONS

Co & Queen, "Humanized antibodies for therapy", 1991 *Nature* 351:501-502.

Coon et al., "Multidrug Resistance Activity in Human Lymphocytes" *Human Immunol.* 32:134 (1991).

Cordon-Cardo et al. "Expression of the Multidrug Resistance Gene Product (P-Glycoprotein) in Human Normal and Tumor Tissues", *J. Histochem. Cytochem* 38:1277 (1990).

Cornwell et al., "Increased Vinblastine Binding to Membrane Vesicles from Multidrug-resistant KB Cells" *J. Bio. Chem.* 261:7921 (1986).

Dillman et al., "Monoclonal Antibodies for Treating Cancer" *Annals. Of Internal Med.* 111(7):592 (1989).

Drach et al., "Subpopulations of Normal Peripheral Blood and Bone Marrow Cells Express a Functional Multidrug Resistant Phenotype" *Blood* 80:2729 (1992).

Efferth et al., "Reciprocal Correlation Betwwen Expression of P-Glycoptotein and Accumulation of Rhodamine 123 in Human Tumors" 1989, *Anti. Cancer Research* 9:1633-1638.

Endicott & Ling, The Biochemistry of P-Glycoprotein-Mediated Multidrug Resistance *Annu. Rev. Biochem,* 58:137 (1989).

Ford et al., "Pharmacology of Drugs that Alter Multidrug Resistance in Cancer" *Pharm. Rev.* 42:155 (1990).

Georges et al. "Detection of P-glycoprotein isoforms by gene-specific monoclonal antibodies" *PNAS (USA)* 87:152-156 (1990).

Gillies et al., "Antigen binding and biological activities of engineered mutant chimeric antibodies with human tumor specificities" *Human Antibod. Hybridons* 1(1):47 (1990).

Gillis, "T-Cell-Derived Lymphokines" 1989, Fundamental Immunology, 2d ed., Raven Press, N.Y., pp. 621-638.

Gottesman & Pastan., "Biochemistry of Multidrug Resistance Mediated by the Multidrug Transporter" *Annu. Rev. Biochem,* 62:385 (1993).

Gros et al., "Isolation and characterization of DNA sequences amplified in multidrug-resistant hamster cells" *Proc. Natl. Acad. Sci. USA* 83:337 (1986).

Gupta et al., "P-Glycoprotein (MDR 1 Gene Product) in Cells of the Immune System: Its Possible Physiologic Role and Alteration in Aging and Human Immunodeficiency Virus-1 (HIV-1) Infection" *J. Clin. Immunol.* 13:289 (1990).

Hamada et al., "Functional role for the 170- to 180-kDa glycoprotein specific to drug-resistant tumor cells as revealed by monoclonal antibodies" *PNAS* 83:7785-7789 (1986).

Hamada et al., "Mouse-Human Chimeric Antibody against the Multidrug Transporter P-Glycoprotein" 1990, *Cancer Res.* 50:3167.

Heike et al., "Monoclonal Anti-P-glycoprotein Antibody-dependant Killing of Multidrug-Resistant Tumor Cells by Human Mononuclear Cells" *Jpn. J. Cancer Res.* 81:1155-61 (1990).

Higgins, "ABC Transporters: from Microorganisms to Man" *Annu. Rev. Cell Biol.* 8:67 (1992).

Hoogenboom et al., "Multi-subunit proteins on the surface of filamentous phage: methodologies for displaying antibody (Fab) heavy and light chains" *Nucleic Acids Research* 19(15):4133-4137, Aug. 11, 1991.

Takeda et al., "Analysis and in vivo disruption of the gene coding for calmodulin in Schizosaccharaomyces pombe" *Proc. Natl. Acad. Sci. USA* 84:3580 (1988).

Klimecki et al., "P-Glycoprotein Expression and Function in Circulating Blood Cells from Normal volunteers" *Blood* 83:2451 (1994).

Kobayashi et al., "Expression and Function of Multidrug Resistance P-Glycoprotein in a Cultured Natural Killer Cell-Rich Population Revealed by Mrk16 Monoclonal Antibody and AHC-52" *Biochem. Pharmacol.* 48:1641 (1994).

Kronke et al., "Cyclosporin A inhibits T-cell growth factor gene expression at the level of mRNA transcription" *Proc. Natl. Sci. USA* 81:5214-5218 (1984).

Kramer et al., "The gapped duplex DNA approach to oligonucleotide-directed mutation construction" *Nucleic Acids Res.* 12:9441-9456 (1984).

Kuwazuru et al., "Expression of the Multidrug Transporter, P-Glycoprotein, in Acute Leukemia Cells and Correlation to Clinical Drug Reistance" *Cancer* 66(5):868 (1990).

Lazar et al., "Transforming Growth Factor α: Mutation of Asparte Acid 47 and Leucine 48 Results In Different Biological Activities" *Molecular and Cellular Biology* 8(3):1247-1252 (1988).

Lokhorst et al., "Advances in the treatment of multiple myeloma" Cancet Treatment Reviews 19:113-128 (1993).

Maino et al., "Rapid Flow Cytometric Method for Measuring Lymphocyte Subset Activation" *Cytometry* 20: 127-133 (1995).

McCafferty et al., "Phage antibodies: filamentous phage displaying antibody variable domains" Nature 348:552-554 (1990).

McDuffie et al., "Morbidity Impact of Rheumatoid Arthritis on Society" *Am. J. Med.* 78(1A): 1-5 (Jan. 21, 1985).

McGrath, "The yeast STE6 gene encodes a homologue of the mammalian multidrug resistance P-glycoprotein" Nature 340:400 (1989).

Mechetner et al., "Efficient inhibition of P-glycoprotein-mediated multidrug resistance with a monoclonal antibody" Proc. Natl. Acad. Sci, USA 89:5824-5828 (1992).

Meyers et al., "Characterization of Monoclonal Anibodies Recognizing a $M_r$ 180,000 P-Glycoprotein: Differential Expression of the $M_4$ 180,000 and $M_r$ 170,000 P-Glycoproteins in Multidrug-resistant Human Tumor Cells" *Cancer Research* 49:3209-3214 (1989).

Mulder et al., "Separation and Functional Analysis of Bone Marrow Cells Separated by Phodamine-123 Fluorescence" 1987, *Exp. Hematol,* 15:99-104.

Müller et al., "Altered Drug-stimulated ATPase Activity in Mutants of the Human Multidrug Resistance Protein" *J. Biol. Chem.* 271:1877-1882 (1996).

Neyfakh et al., "Multidrug-Resistance Phenotype of a Subpopulation of T-Lymphocytes without Drug Selection" *Exp. Cell. Res.* 185:496-505 (1989).

Neyfakh et al., "Use of Fluorescent Dyes as Molecular Probes for the Study of Multidrug Resistance" *Exp. Cell. Res.* 174:168-176 (1988).

Noonan et al., "Quantitiative analysis of MDR1 (multidrug resistance) gene expression in human tumors by polymerase chain reaction" *Proc. Natl. Acad. Sci. USA* 87:7160-7164 (1990).

O'Brien et al., Collateral Sensitivity of Human Multidrug-Resistant Cells to Verapamil is Potentiated by Monoclonal Antibody HYB-241 Recognizing P-glycoprotein *Proc. Amer. Assoc. Cancer Res.* 30:Abs. 2114 (1989).

Pearson et al., "Reversal of Drug Resistance in a Human Colon Cancer Xenograft Expressing MDR1 Complementary DNA by In Vivo Administration of MRK-16 Monoclonal Antibody" J. Nat'l Cancer Inst. 88:1386 (1991).

Ploemacher et al., "Isolation of Hemopoietic Stem Cell Subsets from Murine Bone Marrow: I. Radioprotective Ability of Purified Cell Suspensions Differing in the Proportion of Day-7 and Day-12 CFU-S" *Exp. Hematol* 17:263-266 (1989).

Rittman-Grauer, "Potentiation of vinca toxicity in drug resistant tumors with monoclonal antibody HYB-241" *Proc. Amer. Assoc. Cancer Res.* 31:Abs. 2663- (1990).

Salmon et al., "Multidrug-Resistant Myeloma: Laboratory and Clinical Effects of Verapamil as a Chemosensitizer" *Blood* 78(1):44-50 (1991).

Schluesener et al., "Multidrug transport in human autoimmune T line cells and peripheral blood lymphocytes" *Immunopharmacology* 23:37, Jan.-Feb. 1992.

Schwartz and Datta, "Autoimmunity and Autoimmune Diseases" 1989, *Fundamental Immunology,* 2d ed., Raven Press, N. Y. p. 819-866.

Shen et al., "Multidrug Resistance of DNA-Mediated Transformants is Linked to Transfer of the Human mdr1 Gene" *Molecular and Cellular Biology* 6(11): 4039-4045 (1986).

Spangrade et al., "Resting and activated subsets of mouse multipotent hematopoietic stem cells" 1990, *Proc. Natl. Acad. Sci. USA* 87:7433-7437.

Spangrade, Enrichment of murine haemopoietic stem cells: diverging roads 1989, Eisevier Science Publishers Ltd., UK, p. 344-350.

Srour et al., "Use of an Antibody to the Multidrug Resistance Gene Product, P-Glycoprotein, in the Isolation of Human Hematopoietic Stem Cells" *Experimental Hematology* 20:734 (1992), No. 117.

Srour et al., "Simultaneous Use of CD34, CD15, Anti-HLA-DR and Rhodamine 123 for the Isolation of Precursors of Human Hematopoietic Progenitor Cells" 1990, *Exp. Hemotol.* 18:549, Abstract #3.

Srour et al., Simultanoeus Use of Rhodamine 123, Phycoerythrin, Texas Red, and Allophycocyanin for the Isolation of Human Hematopoietic Progenitor cells 1991, *Cytometry* 12:179-183.

Tamai, "Competitive Interaction of Cyclosporins with vinca Alkaloid-binding site of P-glycoprotein in Multidrug-resistant cells" *J. Biochem, Molec. Biol.* 265:16509 (1990).

Tao et al., "Role of Carbohydrate in the Structure and Effector Functions Mediated by the Human IgG Constant region" *Journal of Immunology* 143(8):2595 (1989).

Thiebaut et al., "Cellular localization of the Multidrug-resistance gene product P-glycoprotein in normal human tissues" *Proc. Natl. Acad. Sci. USA* 84:7735 (1987).

Thorpe, "Antibody Carriers of Cytotoxic Agents in Cancer therapy: A Review" *Monoclonal Antibodies* 84:475-506 (1985).

Tiirikainen et al., "Flow cytometric analysis of P-glycoprotein in normal and leukemic cells" *Ann. Hematol.* 65:124 (1992).

Trail et al., "Cure of Xenografted Human Carcinomas by BR96-Doxorubicin Immunoconjugates" 1993 *Sciences* 261:212-215.

Tsuruo et al., "Inhibition of Multidrug-resistant Human Tumor Growth in Athymic Mice by Anti-P-glycoprotein Monoclonal Antibodies" Jpn. *J. Cancer Res.* 80:627 (1989).

Van der Bliek et al., "Multidrug Resistance" 1989, *Advances in Cancer Research* 52:165.

Van der Sluijs et al., "Marrow Repopulating Cells, But Not CFU-S, Establish Long-term in vitro Hemopoiesis on a Marrow-derived Stromal Layer" 1990, *Exp. Hematol* 18:893-896.

Van Duk et al., "Bispecific Antibodies Reactive with the Multidrug-Resistance-Related Glycoprotein and CD3 Induce Lysis of Multidrug-Resistant Tumor Cells" *Int. J. Cancer* 44:738-743 (1989).

Visser et al., "Purification of Pluripotent Hemopoietic Stem Cells: Past and Present" 1990, *Exp. Hematol.* 18:248-256.

Waldmann, "Monoclonal Antibodies in Diagnosis and Therapy" *Science* 252:1657 (1991).

Weisberg et al., "The Multidrug Resistance Phenotype Confers Immunoglogical Resistance" *J. Exp Med.* 183:2699-2704 (1996).

Winter et al., "Making Antibody by Phage Display Technology" *Annu. Rev. Immunology,* 12:433-455 (1994).

Witkowski et al., "Extrusion of the P Glycoprotein Substrate Rhoamine-123 Distinguishes CD4 Memory T Cell Subsets that Differ in IL-2-Driven IL-4 Production" *J. Immunol.* 153:658 (1994).

FIG. 1A

| | | | | | |
|---|---|---|---|---|---|
| 1 | CCTACTCTAT | TCAGATATTC | TCAGATATTC | TCAGATATTC | AGATCATTTC |
| 51 | TCATTCTCCT | AGGAGTACTC | ACTTCAGGAT | GCAACCAGAT | GTTCGCAGT |
| 101 | TGCAACGGAA | GCCAGAACAT | TCCTCCTGGA | AATTCAACCT | GTTCGCAGT |
| 151 | TTCTCGAGGA | ATCAGCATTC | AGTCAATCCG | GGCCGGGAGC | AGTCATCTGT |
| 201 | GGTGAGGCTG | ATTGGCTGGG | CAGGAACAGC | GCCGGGGCGT | GGGCTGAGCA |
| 251 | CAGCGCTTCG | CTCTCTTTGC | CACAGGAAGC | CTGAGCTCAT | TCGAGTAGCG |
| 301 | GCTCTTCCAA | GCTCAAAGAA | GCAGAGGCCG | CTGTTCGTTT | CCTTTAGGTC |
| 351 | TTTCCACTAA | AGTCGGAGTA | TCTTCTTCCA | AGATTTCACG | TCTTGGTGGC |
| 401 | CGTTCCAAGG | AGCGCGAGGT | CGGGATGGAT | CTTGAAGGGG | ACCGCAATGG |
| 451 | AGGAGCAAAG | AAGAAGAACT | TTTTTAAACT | GAACAATAAA | AGTGAAAAAG |
| 501 | ATAAGAAGGA | AAAGAAACCA | ACTGTCAGTG | TATTTTCAAT | GTTCGCTAT |
| 551 | TCAAATTGGC | TTGACAAGTT | GTATATGGTG | GTGGGAACTT | TGGCTGCCAT |

Fig. 1B

```
601   CATCCATGGG   GCTGGACTTC   CTCTCATGAT   GCTGGTGTTT   GGAGAAATGA
651   CAGATATCTT   TGCAAATGCA   GGAAATTTAG   AAAGATCTGAT   GTCAAACATC
701   ACTAATAGAA   GTGATATCAA   TGATACAGGG   TTCTTCATGA   ATCTGGAGGA
751   AGACATGACC   AGGTATGCCT   ATTATTACAG   TGGAATTGGT   GCTGGGGTGC
801   TGGTTGCTGC   TTACATTCAG   GTTTCATTTT   GGTGCCTGGC   AGCTGGAAGA
851   CAAATACACA   AAATTAGAAA   ACAGTTTTTT   CATGCTATAA   TGCGACAGGA
901   GATAGGCTGG   TTTGATGTGC   ACGATGTTGG   GGAGCTTAAC   ACCCGACTTA
951   CAGATGATGT   CTCCAAGATT   AATGAAGGAA   TTGGTGACAA   AATTGGAATG
1001  TTCTTTCAGT   CAATGGCAAC   ATTTTTCACT   GGGTTTATAG   TAGGATTTAC
1051  ACGTGGTTGG   AAGCTAACCC   TTGTGATTTT   GGCCATCAGT   CCTGTTCTTG
1101  GACTGTCAGC   TGCTGTCTGG   GCAAAGATAC   TATCTTCATT   TACTGATAAA
1151  GAACTCTTAG   CGTATGCAAA   AGCTGGAGCA   GTAGCTGAAG   AGGTCTTGGC
```

Fig. 1C

```
1201  AGCAATTAGA  ACTGTGATTG  CATTGGAGG   ACAAAAGAAA  GAACTTGAAA
1251  GGTACAACAA  AAATTTAGAA  GAAGCTAAAA  GAATTGGGAT  AAAGAAAGCT
1351  TTATGCTCTG  GCCTTCTGGT  ATGGGACCAC  CTTGGTCCTC  TCAGGGGAAT
1401  ATTCTATTGG  ACAAGTACTC  ACTGTATTCT  TTTCTGTATT  AATTGGGCT
1451  TTTAGTGTTG  GACAGGCATC  TCCAAGCATT  GAAGCATTTG  CAAATGCAAG
1501  AGGAGCAGCT  TATGAAATCT  TCAAGATAAT  TGATAATAAG  CCAAGTATTG
1551  ACAGCTATTC  GAAGAGTGGG  CACAAACCAG  ATAATATTAA  GGGAAATTTG
1601  GAATTCAGAA  ATGTTCACTT  CAGTTACCCA  TCTCGAAAAG  AAGTTAAGAT
1651  CTTGAAGGGC  CTGAACCTGA  AGGTGCAGAG  TGGGCAGACG  GTGGCCCTGG
1701  TTGGAAACAG  TGGCTGTGGG  AAGAGCACAA  CAGTCCAGCT  GATGCAGAGG
1751  CTCTATGACC  CCACAGAGGG  GATGGTCAGT  GTTGATGGAC  AGGATATTAG
1801  GACCATAAAT  GTAAGGTTTC  TACGGGAAAT  CATTGGTGTG  GTGAGTCAGG
```

Fig. 1D

```
1851  AACCTGTATT  GTTTGCCACC  ACGATAGCTG  AAAACATTCG  CTATGGCCGT
1901  GAAAATGTCA  CCATGGATGA  GATTGAGAAA  GCTGTCAAGG  AAGCCAATGC
1951  CTATGACTTT  ATCATGAAAC  TGCCTCATAA  ATTTGACACC  CTGGTTGGAG
2051  CGTGCCCTGG  TTCGCAACCC  CAAGATCCTC  CTGCTGGATG  AGGCCACGTC
2101  AGCCTTGGAC  ACAGAAAGCG  AAGCAGTGGT  TCAGGTGGCT  CTGGATAAGG
2151  CCAGAAAAGG  TCGGACCACC  ATTGTGATAG  CTCATCGTTT  GTCTACAGTT
2201  CGTAATGCTG  ACGTCATCGC  TGGTTTCGAT  GATGGAGTCA  TTGTGGAGAA
2251  AGGAAATCAT  GATGAACTCA  TGAAAGAGAA  AGGCATTAC  TTCAAACTTG
2301  TCACAATGCA  GACAGCAGGA  AATGAAGTTG  AATTAGAAAA  TGCAGCTGAT
2351  GAATCCAAAA  GTGAAATTGA  TGCCCTTGGAA  ATGTCTTCAA  ATGATTCAAG
2401  ATCCAGTCTA  ATAAGAAAAA  GATCAACTCG  TAGGAGTGTC  CGTGGATCAC
2451  AAGCCCAAGA  CAGAAAGCTT  AGTACCAAAG  AGGCTCTGGA  TGAAAGTATA
```

Fig. 1E

```
2501  CCTCCAGTTT  CCTTTTGGAG  GATTATGAAG  CTAAATTTAA  CTGAATGGCC
2551  TTATTTGTT   GTTGGTGTAT  TTTGTGCCAT  TATAAATGGA  GGCCTGCAAC
2601  CAGCATTGC   AATAATATTT  TCAAAGATTA  TAGGGGTTTT  TACAAGAATT
2651  GATGATCCTG  AAACAAAACG  ACAGAATAGT  AACTTGTTTT  CACTATTGTT
2701  TCTAGCCCTT  GGAATTATTT  CTTTTRTTAC  ATTTTTCCTT  CAGGGTTTCA
2751  CATTTGGCAA  AGCTCCAGAG  ATCCTCACCA  AGCGGCTCCG  ATACATGTT
2801  TTCCGATCCA  TGCTCAGACA  GGATGTGAGT  TGGTTTGATG  ACCCTAAAAA
2851  CACCACTGGA  GCATTGACTA  CCAGGCTCGC  CAATGATGCT  GCTCAAGTTA
2901  AAGGGGCTAT  AGGTTCCAGG  CTTGCTGTAA  TTACCCAGAA  TATAGCAAAT
2951  CTTGGGACAG  GAATAATTAT  ATCCTTCATC  TATGGTTGGC  AACTAACACT
3001  GTTACTCTTA  GCAATTGTAC  CCATCATTGC  AATAGCAGGA  GTTGTTGAAA
3051  TGAAAATGTT  GTCTGGACAA  GCACTGAAAG  ATAAGAAAGA  ACTAGAAGGT
```

Fig. 1F

```
3101  GCTGGGAAGA  TCCCTACTGA  AGCAATAGAA  CCGTTGTTTC
3151  TTTGACTCAG  GAGCAGAAGT  TTGAACATAT  AGTTTGCAGG
3201  TACCATACAG  AAACTCTTTG  AGGAAAGCAC  AATTACATTT
3251  TCCTTCACCC  AGGCAATGAT  GTATTTTTCC  GTTTCCGGTT
3301  TGGAGCCTAC  TTGGTGGCAC  ATAAACTCAT  GATGTTCTGT
3351  TCATTTGCTC  CTGACTATGC  CAAAGCCAAA  CCCACATCAT
3451  CATGATCATT  GAAAAAACCC  CTTTGATTGA  ACGGAAGGCC
3501  TAATGCCGAA  CACATTGGAA  GGAAATGTCA  AGTTGTATTC
3551  AACTATCCCA  CCCGACCGGA  CATCCCAGTG  TGAGCCTGGA
3601  GGTGAAGAAG  GGCCAGACGC  TGGCTCTGGT  GGCTGTGGGA
3651  AGAGCACAGT  GGTCCAGCTC  CTGGAGCGGG  CTTGGCAGGG
3701  AAAGTGCTGC  TTGATGGCAA  AGAAATAAAG  CGACTGAATG  TTCAGTGGCT
```

Fig. 1G

| | | | | |
|---|---|---|---|---|
| 3751 | CCGAGCACAC | CTGGGCATCG | TGTCCCAGGA | GCCCATCCTG | TTTGACTGCA |
| 3801 | GCATTGCTGA | GAACATTGCC | TATGGAGACA | ACAGCCGGGT | GGTGTCACAG |
| 3851 | GAAGAGATCG | TGAGGGCAGC | AAAGGAGGCC | AACATACATG | CCTTCATCGA |
| 3901 | GTCACTGCCT | AATAAATATA | GCACTAAAGT | AGGAGACAAA | GGAACTCAGC |
| 3951 | TCTCTGGTGG | CCAGAAACAA | CGCATTGCCA | TAGCTCGTGC | CCTTGTTAGA |
| 4001 | CAGCCTCATA | TTTTGCTTTT | GGATGAAGCC | ACGTCAGCTC | TGGATACAGA |
| 4051 | AAGTGAAAAG | GTTGTCCAAG | AAGCCCTGGA | CAAAGCCAGA | GAAGGCCGCA |
| 4101 | CCTGCATTGT | GATTGCTCAC | CGCCTGTCCA | CCATCCAGAA | TGCAGACTTA |
| 4151 | ATAGTGGTGT | TTCAGAATGG | CAGAGTCAAG | GAGCATGGCA | CGCATCAGCA |
| 4201 | GCTGCTGGCA | CAGAAAGGCA | TCTATTTTTC | AATGGTCAGT | GTCCAGGCTG |
| 4251 | GAACAAAGCG | CCAGTGAACT | CTGACTGTAT | GAGATGTTAA | ATACTTTTA |
| 4301 | ATATTTGTTT | AGATATGACA | TTTATTCAAA | GTTAAAAGCA | AACACTTACA |

Fig. 1H

```
4351  GAATTATGAA  GAGGTATCTG  TTTAACATTT  CCTCAGTCAA  GTTCAGAGTC
4401  TTCAGAGACT  TCGTAATTAA  AGGAACAGAG  TGAGAGACAT  CATCAAGTGG
4451  AGAGAAATCA  TAGTTTAAAC  TGCATTATAA  ATTTATAAAC  AGAATTAAAG
4501  TAGATTTAA   AAGATAAAAT  GTGTAATTTT  GTTTATATTT  TCCCATTTGG
4551  ACTGTAACTG  ACTGCCTTGC  TAAAAGATTA  TAGAAGTAGC  AAAAAGTATT
4601  GAAATGTTTG  CATAAAGTGT  CTATAATAAA  ACTAAACTTT  CATGTGAAAA
4651  AAAAAAAAA   AAAAAAAAA
```

FIG. 2A
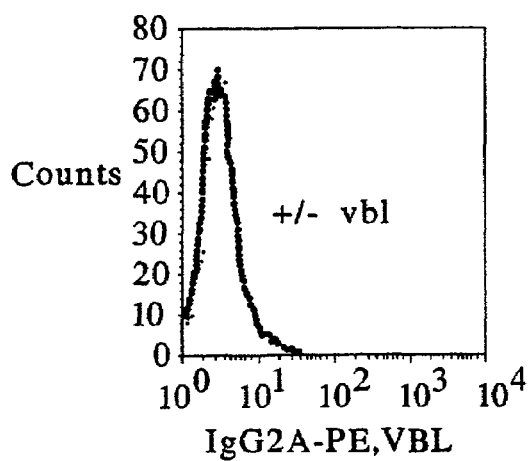
IgG2A-PE,VBL
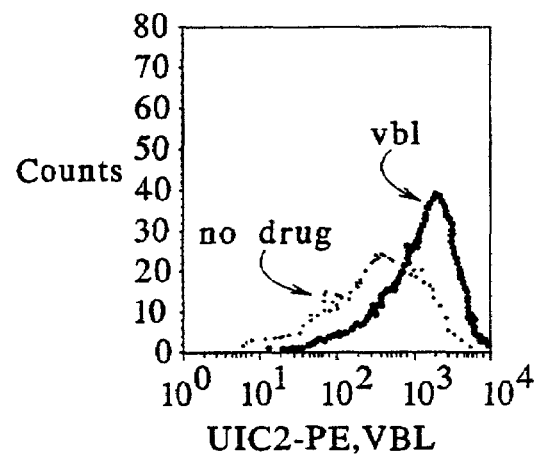
UIC2-PE,VBL
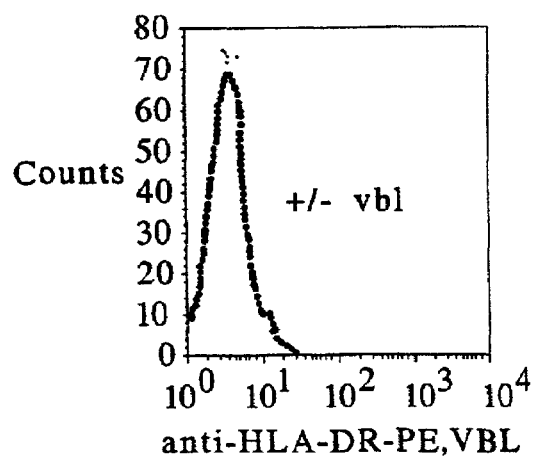
anti-HLA-DR-PE,VBL
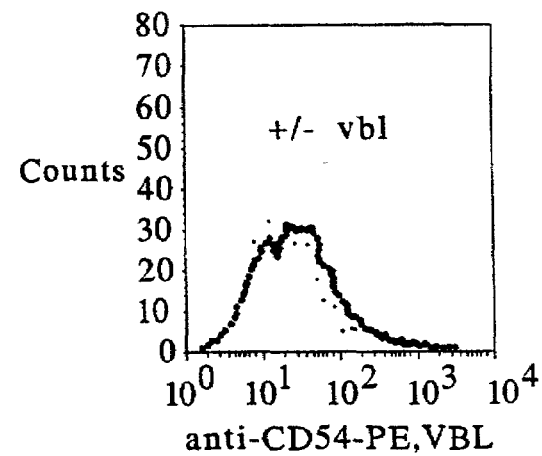
anti-CD54-PE,VBL

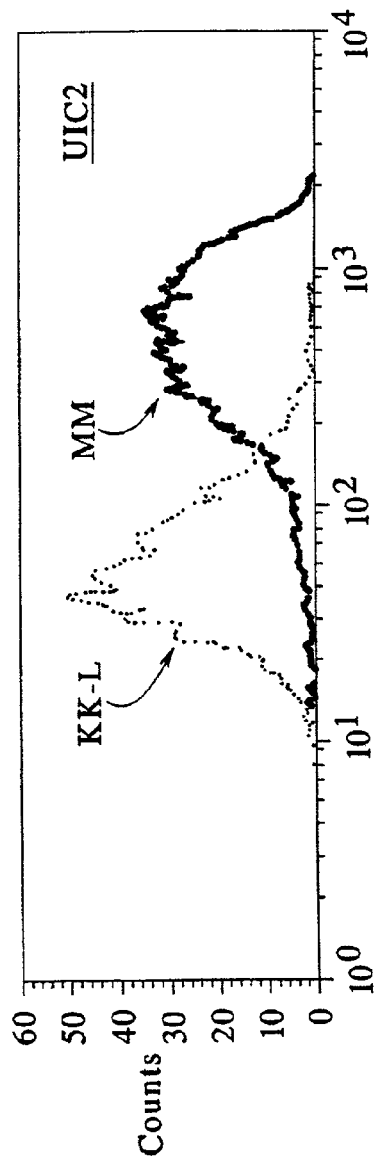
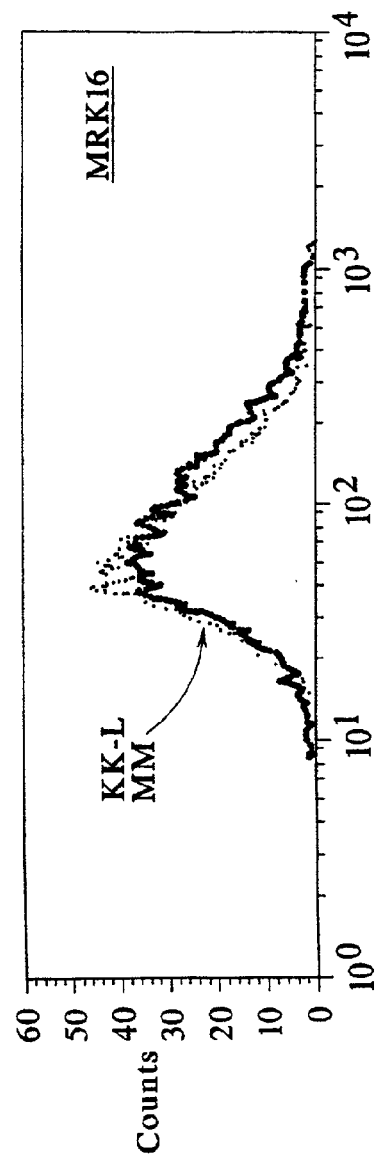
FIG. 5A
FIG. 5B

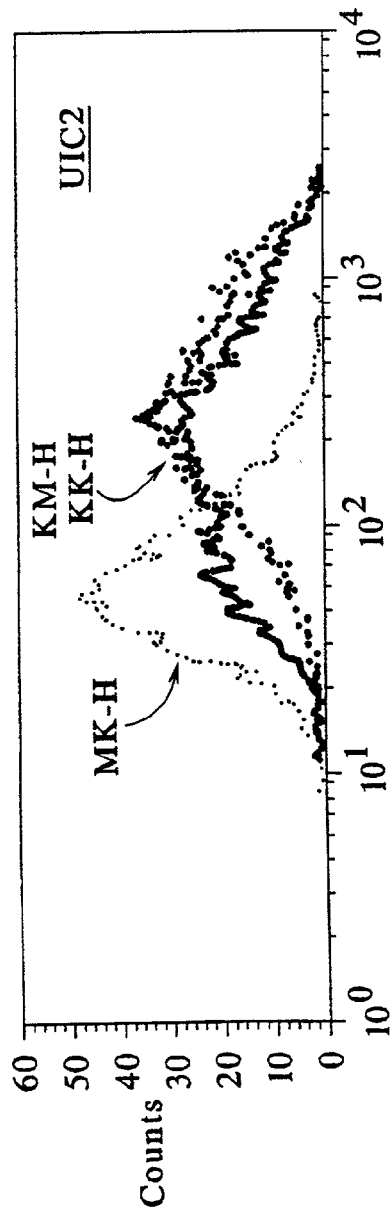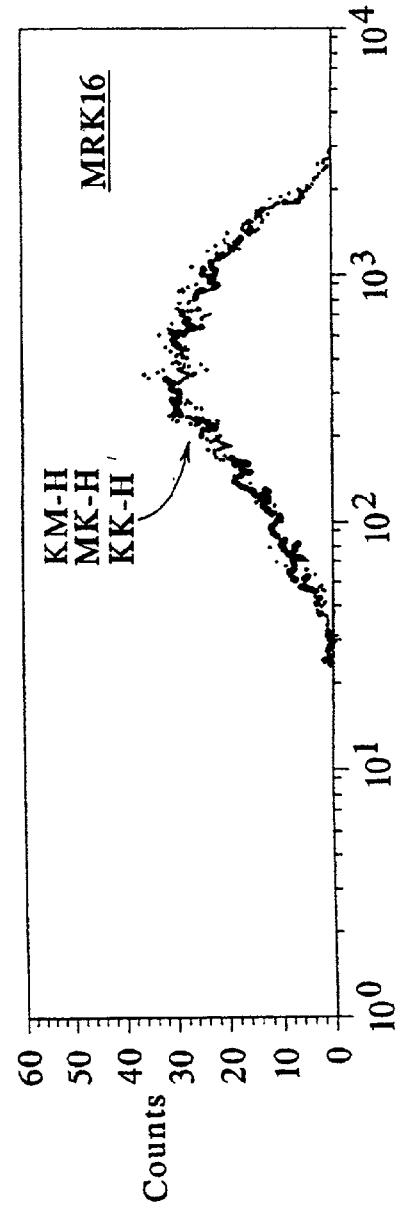
FIG. 5C
FIG. 5D

SN-38: UIC2 SHIFT IN MCF7-40F P.4 BREAST CARCINOMA
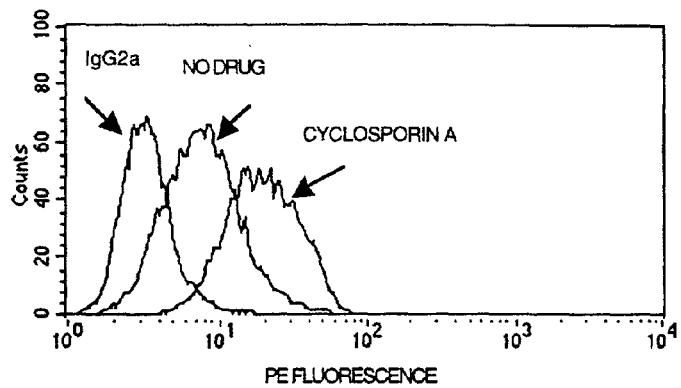
CYCLOSPORIN A (positive control)
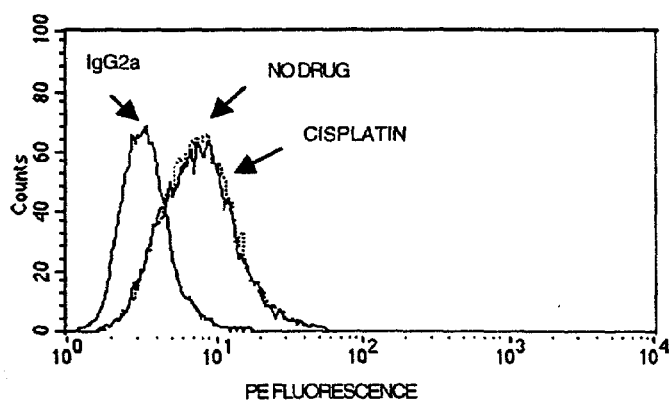
CISPLATIN (negative control)
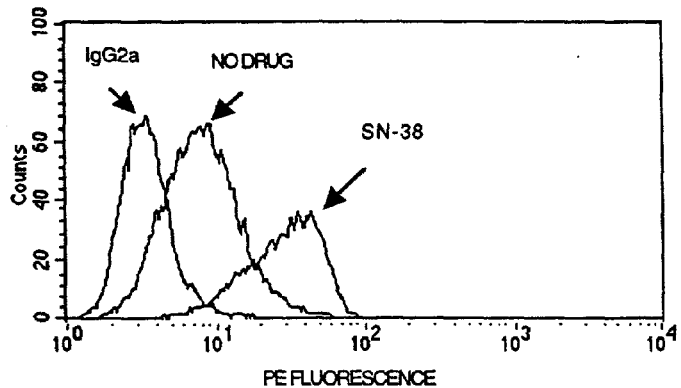
SN-38
*FIG. 12*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 4669 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: 5'UTR
      (B) LOCATION: 1..424

(ix) FEATURE:
      (A) NAME/KEY: CDS
      (B) LOCATION: 425..4264

(ix) FEATURE:
      (A) NAME/KEY: 3'UTR
      (B) LOCATION: 4265..4669

(xi) SEQUENCE DESCRIPTION: SEQ ID NO: 1:

```
CCTACTCTAT TCAGATATTC TCCAGATTCC TAAAGATTAG AGATCATTTC TCATTCTCCT        60

AGGAGTACTC ACTTCAGGAA GCAACCAGAT AAAAGAGAGG TGCAACGGAA GCCAGAACAT       120

TCCTCCTGGA AATTCAACCT GTTTCGCAGT TTCTCGAGGA ATCAGCATTC AGTCAATCCG       180

GGCCGGGAGC AGTCATCTGT GGTGAGGCTG ATTGGCTGGG CAGGAACAGC GCCGGGGCGT       240

GGGCTGAGCG CAGCGCTTCG CTCTCTTTGC CACAGGAAGC CTGAGCTCAT TCGAGTAGCG       300

GCTCTTCCAA GCTCAAAGAA GCAGAGGCCG CTGTTCGTTT CCTTTAGGTC TTTCCACTAA       360

AGTCGGAGTA TCTTCTTCCA AGATTTCACG TCTTGGTGGC CGTTCCAAGG AGCGCGAGGT       420

CGGG ATG GAT CTT GAA GGG GAC CGC AAT GGA GGA GCA AAG AAG AAG AAC       469
     Met Asp Leu Glu Gly Asp Arg Asn Gly Gly Ala Lys Lys Lys Asn
      1               5                  10                  15

TTT TTT AAA CTG AAC AAT AAA AGT GAA AAA GAT AAG AAG GAA AAG AAA       517
Phe Phe Lys Leu Asn Asn Lys Ser Glu Lys Asp Lys Lys Glu Lys Lys
                20                  25                  30
```

-continued

| | |
|---|---|
| CCA ACT GTC AGT GTA TTT TCA ATG TTT CGC TAT TCA AAT TGG CTT GAC<br>Pro Thr Val Ser Val Phe Ser Met Phe Arg Tyr Ser Asn Trp Leu Asp<br>              35                    40                    45 | 565 |
| AAG TTG TAT ATG GTG GTG GGA ACT TTG GCT GCC ATC ATC CAT GGG GCT<br>Lys Leu Tyr Met Val Val Gly Thr Leu Ala Ala Ile Ile His Gly Ala<br>            50                    55                    60 | 613 |
| GGA CTT CCT CTC ATG ATG CTG GTG TTT GGA GAA ATG ACA GAT ATC TTT<br>Gly Leu Pro Leu Met Met Leu Val Phe Gly Glu Met Thr Asp Ile Phe<br>65                    70                    75 | 661 |
| GCA AAT GCA GGA AAT TTA GAA GAT CTG ATG TCA AAC ATC ACT AAT AGA<br>Ala Asn Ala Gly Asn Leu Glu Asp Leu Met Ser Asn Ile Thr Asn Arg<br>80                    85                    90                    95 | 709 |
| AGT GAT ATC AAT GAT ACA GGG TTC TTC ATG AAT CTG GAG GAA GAC ATG<br>Ser Asp Ile Asn Asp Thr Gly Phe Phe Met Asn Leu Glu Glu Asp Met<br>                 100                 105                110 | 757 |
| ACC AGG TAT GCC TAT TAT TAC AGT GGA ATT GGT GCT GGG GTG CTG GTT<br>Thr Arg Tyr Ala Tyr Tyr Tyr Ser Gly Ile Gly Ala Gly Val Leu Val<br>               115                   120                 125 | 805 |
| GCT GCT TAC ATT CAG GTT TCA TTT TGG TGC CTG GCA GCT GGA AGA CAA<br>Ala Ala Tyr Ile Gln Val Ser Phe Trp Cys Leu Ala Ala Gly Arg Gln<br>             130                 135                140 | 853 |
| ATA CAC AAA ATT AGA AAA CAG TTT TTT CAT GCT ATT ATG CGA CAG GAG<br>Ile His Lys Ile Arg Lys Gln Phe Phe His Ala Ile Met Arg Gln Glu<br>       145                   150 | 901 |
| ATA GGC TGG TTT GAT GTG CAC GAT GTT GGG GAG CTT AAC ACC CGA CTT<br>Ile Gly Trp Phe Asp Val His Asp Val Gly Glu Leu Asn Thr Arg Leu<br>160                   165                 170                175 | 949 |
| ACA GAT GAT GTC TCC AAG ATT AAT GAA GGA ATT GGT GAC AAA ATT GGA<br>Thr Asp Asp Val Ser Lys Ile Asn Glu Gly Ile Gly Asp Lys Ile Gly<br>               180                 185                190 | 997 |
| ATG TTC TTT CAG TCA ATG GCA ACA TTT TTC ACT GGG TTT ATA GTA GGA<br>Met Phe Phe Gln Ser Met Ala Thr Phe Phe Thr Gly Phe Ile Val Gly<br>             195                 200                205 | 1045 |
| TTT ACA CGT GGT TGG AAG CTA ACC CTT GTG ATT TTG GCC ATC AGT CCT<br>Phe Thr Arg Gly Trp Lys Leu Thr Leu Val Ile Leu Ala Ile Ser Pro<br>             210                 215                220 | 1093 |
| GTT CTT GGA CTG TCA GCT GCT GTC TGG GCA AAG ATA CTA TCT TCA TTT<br>Val Leu Gly Leu Ser Ala Ala Val Trp Ala Lys Ile Leu Ser Ser Phe<br>225                   230                 235 | 1141 |
| ACT GAT AAA GAA CTC TTA GCG TAT GCA AAA GCT GGA GCA GTA GCT GAA<br>Thr Asp Lys Glu Leu Leu Ala Tyr Ala Lys Ala Gly Ala Val Ala Glu<br>240                   245                 250                255 | 1189 |
| GAG GTC TTG GCA GCA ATT AGA ACT GTG ATT GCA TTT GGA GGA CAA AAG<br>Glu Val Leu Ala Ala Ile Arg Thr Val Ile Ala Phe Gly Gly Gln Lys<br>             260                 265                270 | 1237 |
| AAA GAA CTT GAA AGG TAC AAC AAA AAT TTA GAA GAA GCT AAA AGA ATT<br>Lys Glu Leu Glu Arg Tyr Asn Lys Asn Leu Glu Glu Ala Lys Arg Ile<br>             275                 280                285 | 1285 |
| GGG ATA AAG AAA GCT ATT ACA GCC AAT ATT TCT ATA GGT GCT GCT TTC<br>Gly Ile Lys Lys Ala Ile Thr Ala Asn Ile Ser Ile Gly Ala Ala Phe<br>             290                 295                300 | 1333 |
| CTG CTG ATC TAT GCA TCT TAT GCT GTG GCC TTC TGG TAT GGG ACC ACC<br>Leu Leu Ile Tyr Ala Ser Tyr Ala Val Ala Phe Trp Tyr Gly Thr Thr<br>305                   310                 315 | 1381 |
| TTG GTC CTC TCA GGG GAA TAT TCT ATT GGA CAA GTA CTC ACT GTA TTC<br>Leu Val Leu Ser Gly Glu Tyr Ser Ile Gly Gln Val Leu Thr Val Phe<br>320                   325                 330                335 | 1429 |
| TTT TCT GTA TTA ATT GGG GCT TTT AGT GTT GGA CAG GCA TCT CCA AGC<br>Phe Ser Val Leu Ile Gly Ala Phe Ser Val Gly Gln Ala Ser Pro Ser | 1477 |

```
                    340                 345                 350
ATT GAA GCA TTT GCA AAT GCA AGA GGA GCA GCT TAT GAA ATC TTC AAG     1525
Ile Glu Ala Phe Ala Asn Ala Arg Gly Ala Ala Tyr Glu Ile Phe Lys
                355                 360                 365

ATA ATT GAT AAT AAG CCA AGT ATT GAC AGC TAT TCG AAG AGT GGG CAC     1573
Ile Ile Asp Asn Lys Pro Ser Ile Asp Ser Tyr Ser Lys Ser Gly His
            370                 375                 380

AAA CCA GAT AAT ATT AAG GGA AAT TTG GAA TTC AGA AAT GTT CAC TTC     1621
Lys Pro Asp Asn Ile Lys Gly Asn Leu Glu Phe Arg Asn Val His Phe
        385                 390                 395

AGT TAC CCA TCT CGA AAA GAA GTT AAG ATC TTG AAG GGC CTG AAC CTG     1669
Ser Tyr Pro Ser Arg Lys Glu Val Lys Ile Leu Lys Gly Leu Asn Leu
400                 405                 410                 415

AAG GTG CAG AGT GGG CAG ACG GTG GCC CTG GTT GGA AAC AGT GGC TGT     1717
Lys Val Gln Ser Gly Gln Thr Val Ala Leu Val Gly Asn Ser Gly Cys
                420                 425                 430

GGG AAG AGC ACA ACA GTC CAG CTG ATG CAG AGG CTC TAT GAC CCC ACA     1765
Gly Lys Ser Thr Thr Val Gln Leu Met Gln Arg Leu Tyr Asp Pro Thr
            435                 440                 445

GAG GGG ATG GTC AGT GTT GAT GGA CAG GAT ATT AGG ACC ATA AAT GTA     1813
Glu Gly Met Val Ser Val Asp Gly Gln Asp Ile Arg Thr Ile Asn Val
        450                 455                 460

AGG TTT CTA CGG GAA ATC ATT GGT GTG GTG AGT CAG GAA CCT GTA TTG     1861
Arg Phe Leu Arg Glu Ile Ile Gly Val Val Ser Gln Glu Pro Val Leu
465                 470                 475

TTT GCC ACC ACG ATA GCT GAA AAC ATT CGC TAT GGC CGT GAA AAT GTC     1909
Phe Ala Thr Thr Ile Ala Glu Asn Ile Arg Tyr Gly Arg Glu Asn Val
480                 485                 490                 495

ACC ATG GAT GAG ATT GAG AAA GCT GTC AAG GAA GCC AAT GCC TAT GAC     1957
Thr Met Asp Glu Ile Glu Lys Ala Val Lys Glu Ala Asn Ala Tyr Asp
                500                 505                 510

TTT ATC ATG AAA CTG CCT CAT AAA TTT GAC ACC CTG GTT GGA GAG AGA     2005
Phe Ile Met Lys Leu Pro His Lys Phe Asp Thr Leu Val Gly Glu Arg
            515                 520                 525

GGG GCC CAG TTG AGT GGT GGG CAG AAG CAG AGG ATC GCC ATT GCA CGT     2053
Gly Ala Gln Leu Ser Gly Gly Gln Lys Gln Arg Ile Ala Ile Ala Arg
        530                 535                 540

GCC CTG GTT CGC AAC CCC AAG ATC CTC CTG CTG GAT GAG GCC ACG TCA     2101
Ala Leu Val Arg Asn Pro Lys Ile Leu Leu Leu Asp Glu Ala Thr Ser
545                 550                 555

GCC TTG GAC ACA GAA AGC GAA GCA GTG GTT CAG GTG GCT CTG GAT AAG     2149
Ala Leu Asp Thr Glu Ser Glu Ala Val Val Gln Val Ala Leu Asp Lys
560                 565                 570                 575

GCC AGA AAA GGT CGG ACC ACC ATT GTG ATA GCT CAT CGT TTT GCT ACA     2197
Ala Arg Lys Gly Arg Thr Thr Ile Val Ile Ala His Arg Phe Ala Thr
                580                 585                 590

GTT CGT AAT GCT GAC GTC ATC GCT GGT TTC GAT GAT GGA GTC ATT GTG     2245
Val Arg Asn Ala Asp Val Ile Ala Gly Phe Asp Asp Gly Val Ile Val
            595                 600                 605

GAG AAA GGA AAT CAT GAT GAA CTC ATG AAA GAG AAA GGC ATT TAC TTC     2293
Glu Lys Gly Asn His Asp Glu Leu Met Lys Glu Lys Gly Ile Tyr Phe
        610                 615                 620

AAA CTT GTC ACA ATG CAG ACA GCA GGA AAT GAA GTT GAA TTA GAA AAT     2341
Lys Leu Val Thr Met Gln Thr Ala Gly Asn Glu Val Glu Leu Glu Asn
625                 630                 635

GCA GCT GAT GAA TCC AAA AGT GAA ATT GAT GCC TTG GAA ATG TCT TCA     2389
Ala Ala Asp Glu Ser Lys Ser Glu Ile Asp Ala Leu Glu Met Ser Ser
640                 645                 650                 655

AAT GAT TCA AGA TCC AGT CTA ATA AGA AAA AGA TCA ACT CGT AGG AGT     2437
```

```
                 Asn Asp Ser Arg Ser Ser Leu Ile Arg Lys Arg Ser Thr Arg Arg Ser
                             660                 665                 670

GTC CGT GGA TCA CAA GCC CAA CAC AGA AAG CTT AGT ACC AAA GAG GCT          2485
Val Arg Gly Ser Gln Ala Gln His Arg Lys Leu Ser Thr Lys Glu Ala
            675                 680                 685

CTG GAT GAA AGT ATA CCT CCA GTT TCC TTT TGG AGG ATT ATG AAG CTA          2533
Leu Asp Glu Ser Ile Pro Pro Val Ser Phe Trp Arg Ile Met Lys Leu
            690                 695                 700

AAT TTA ACT GAA TGG CCT TAT TTT GTT GTT GGT GTA TTT TGT GCC ATT          2581
Asn Leu Thr Glu Trp Pro Tyr Phe Val Val Gly Val Phe Cys Ala Ile
        705                 710                 715

ATA AAT GGA GGC CTG CAA CCA GCA TTT GCA ATA ATA TTT TCA AAG ATT          2629
Ile Asn Gly Gly Leu Gln Pro Ala Phe Ala Ile Ile Phe Ser Lys Ile
720                 725                 730                 735

ATA GGG GTT TTT ACA AGA ATT GAT GAT CCT GAA ACA AAA CGA CAG AAT          2677
Ile Gly Val Phe Thr Arg Ile Asp Asp Pro Glu Thr Lys Arg Gln Asn
                740                 745                 750

AGT AAC TTG TTT TCA CTA TTG TTT CTA GCC CTT GGA ATT ATT TCT TTT          2725
Ser Asn Leu Phe Ser Leu Leu Phe Leu Ala Leu Gly Ile Ile Ser Phe
            755                 760                 765

ATT ACA TTT TTC CTT CAG GGT TTC ACA TTT GGC AAA GCT GGA GAG ATC          2773
Ile Thr Phe Phe Leu Gln Gly Phe Thr Phe Gly Lys Ala Gly Glu Ile
        770                 775                 780

CTC ACC AAG CGG CTC CGA TAC ATG GTT TTC CGA TCC ATG CTC AGA CAG          2821
Leu Thr Lys Arg Leu Arg Tyr Met Val Phe Arg Ser Met Leu Arg Gln
        785                 790                 795

GAT GTG AGT TGG TTT CAT GAC CCT AAA AAC ACC ACT GGA GCA TTG ACT          2869
Asp Val Ser Trp Phe His Asp Pro Lys Asn Thr Thr Gly Ala Leu Thr
800                 805                 810                 815

ACC AGG CTC GCC AAT GAT GCT GCT CAA GTT AAA GGG GCT ATA GGT TCC          2917
Thr Arg Leu Ala Asn Asp Ala Ala Gln Val Lys Gly Ala Ile Gly Ser
                820                 825                 830

AGG CTT GCT GTA ATT ACC CAG AAT ATA GCA AAT CTT GGG ACA GGA ATA          2965
Arg Leu Ala Val Ile Thr Gln Asn Ile Ala Asn Leu Gly Thr Gly Ile
            835                 840                 845

ATT ATA TCC TTC ATC TAT GGT TGG CAA CTA ACA CTG TTA CTC TTA GCA          3013
Ile Ile Ser Phe Ile Tyr Gly Trp Gln Leu Thr Leu Leu Leu Leu Ala
        850                 855                 860

ATT GTA CCC ATC ATT GCA ATA GCA GGA GTT GTT GAA ATG AAA ATG TTT          3061
Ile Val Pro Ile Ile Ala Ile Ala Gly Val Val Glu Met Lys Met Phe
    865                 870                 875

GCT GGA CAA GCA CTG AAA GAT AAG AAA GAA CTA GAA GGT GCT GGG AAG          3109
Ala Gly Gln Ala Leu Lys Asp Lys Lys Glu Leu Glu Gly Ala Gly Lys
880                 885                 890                 895

ATC GCT ACT GAA GCA ATA GAA AAC TTC CGA ACC GTT GTT TCT TTG ACT          3157
Ile Ala Thr Glu Ala Ile Glu Asn Phe Arg Thr Val Val Ser Leu Thr
                900                 905                 910

CAG GAG CAG AAG TTT GAA CAT ATG TAT GCT CAG AGT TTG CAG GTA CCA          3205
Gln Glu Gln Lys Phe Glu His Met Tyr Ala Gln Ser Leu Gln Val Pro
            915                 920                 925

TAC AGA AAC TCT TTG AGG AAA GCA CAC ATC TTT GGA ATT ACA TTT TCC          3253
Tyr Arg Asn Ser Leu Arg Lys Ala His Ile Phe Gly Ile Thr Phe Ser
        930                 935                 940

TTC ACC CAG GCA ATG ATG TAT TTT TCC TAT GCT GGA TGT TTC CGG TTT          3301
Phe Thr Gln Ala Met Met Tyr Phe Ser Tyr Ala Gly Cys Phe Arg Phe
    945                 950                 955

GGA GCC TAC TTG GTG GCA CAT AAA CTC ATG AGC TTT GAG GAT GTT CTG          3349
Gly Ala Tyr Leu Val Ala His Lys Leu Met Ser Phe Glu Asp Val Leu
960                 965                 970                 975
```

| | | |
|---|---|---|
| TTA GTA TTT TCA GCT GTT GTC TTT GGT GCC ATG GCC GTG GGG CAA GTC<br>Leu Val Phe Ser Ala Val Val Phe Gly Ala Met Ala Val Gly Gln Val<br>              980               985                  990 | | 3397 |
| AGT TCA TTT GCT CCT GAC TAT GCC AAA GCC AAA ATA TCA GCA GCC CAC<br>Ser Ser Phe Ala Pro Asp Tyr Ala Lys Ala Lys Ile Ser Ala Ala His<br>              995              1000              1005 | | 3445 |
| ATC ATC ATG ATC ATT GAA AAA ACC CCT TTG ATT GAC AGC TAC AGC ACG<br>Ile Ile Met Ile Ile Glu Lys Thr Pro Leu Ile Asp Ser Tyr Ser Thr<br>    1010                      1015                      1020 | | 3493 |
| GAA GGC CTA ATG CCG AAC ACA TTG GAA GGA AAT GTC ACA TTT GGT GAA<br>Glu Gly Leu Met Pro Asn Thr Leu Glu Gly Asn Val Thr Phe Gly Glu<br>        1025                      1030                  1035 | | 3541 |
| GTT GTA TTC AAC TAT CCC ACC CGA CCG GAC ATC CCA GTG CTT CAG GGA<br>Val Val Phe Asn Tyr Pro Thr Arg Pro Asp Ile Pro Val Leu Gln Gly<br>1040                      1045                    1050                  1055 | | 3589 |
| CTG AGC CTG GAG GTG AAG AAG GGC CAG ACG CTG GCT CTG GTG GGC AGC<br>Leu Ser Leu Glu Val Lys Lys Gly Gln Thr Leu Ala Leu Val Gly Ser<br>              1060                      1065                    1070 | | 3637 |
| AGT GGC TGT GGG AAG AGC ACA GTG GTC CAG CTC CTG GAG CGG TTC TAC<br>Ser Gly Cys Gly Lys Ser Thr Val Val Gln Leu Leu Glu Arg Phe Tyr<br>            1075                      1080                    1085 | | 3685 |
| GAC CCC TTG GCA GGG AAA GTG CTG CTT GAT GGC AAA GAA ATA AAG CGA<br>Asp Pro Leu Ala Gly Lys Val Leu Leu Asp Gly Lys Glu Ile Lys Arg<br>        1090                      1095                  1100 | | 3733 |
| CTG AAT GTT CAG TGG CTC CGA GCA CAC CTG GGC ATC GTG TCC CAG GAG<br>Leu Asn Val Gln Trp Leu Arg Ala His Leu Gly Ile Val Ser Gln Glu<br>        1105                      1110                  1115 | | 3781 |
| CCC ATC CTG TTT GAC TGC AGC ATT GCT GAG AAC ATT GCC TAT GGA GAC<br>Pro Ile Leu Phe Asp Cys Ser Ile Ala Glu Asn Ile Ala Tyr Gly Asp<br>1120                      1125                    1130                  1135 | | 3829 |
| AAC AGC CGG GTG GTG TCA CAG GAA GAG ATC GTG AGG GCA GCA AAG GAG<br>Asn Ser Arg Val Val Ser Gln Glu Glu Ile Val Arg Ala Ala Lys Glu<br>            1140                      1145                    1150 | | 3877 |
| GCC AAC ATA CAT GCC TTC ATC GAG TCA CTG CCT AAT AAA TAT AGC ACT<br>Ala Asn Ile His Ala Phe Ile Glu Ser Leu Pro Asn Lys Tyr Ser Thr<br>              1155                      1160                    1165 | | 3925 |
| AAA GTA GGA GAC AAA GGA ACT CAG CTC TCT GGT GGC CAG AAA CAA CGC<br>Lys Val Gly Asp Lys Gly Thr Gln Leu Ser Gly Gly Gln Lys Gln Arg<br>        1170                      1175                  1180 | | 3973 |
| ATT GCC ATA GCT CGT CGC CTT GTT AGA CAG CCT CAT ATT TTG CTT TTG<br>Ile Ala Ile Ala Arg Arg Leu Val Arg Gln Pro His Ile Leu Leu Leu<br>        1185                      1190                  1195 | | 4021 |
| GAT GAA GCC ACG TCA GCT CTG GAT ACA GAA AGT GAA AAG GTT GTC CAA<br>Asp Glu Ala Thr Ser Ala Leu Asp Thr Glu Ser Glu Lys Val Val Gln<br>1200                      1205                    1210                  1215 | | 4069 |
| GAA GCC CTG GAC AAA GCC AGA GAA GGC CGC ACC TGC ATT GTG ATT GCT<br>Glu Ala Leu Asp Lys Ala Arg Glu Gly Arg Thr Cys Ile Val Ile Ala<br>              1220                      1225                    1230 | | 4117 |
| CAC CGC CTG TCC ACC ATC CAG AAT GCA GAC TTA ATA GTG GTG TTT CAG<br>His Arg Leu Ser Thr Ile Gln Asn Ala Asp Leu Ile Val Val Phe Gln<br>            1235                      1240                    1245 | | 4165 |
| AAT GGC AGA GTC AAG GAG CAT GGC ACG CAT CAG CAG CTG CTG GCA CAG<br>Asn Gly Arg Val Lys Glu His Gly Thr His Gln Gln Leu Leu Ala Gln<br>        1250                      1255                  1260 | | 4213 |
| AAA GGC ATC TAT TTT TCA ATG GTC AGT GTC CAG GCT GGA ACA AAG CGC<br>Lys Gly Ile Tyr Phe Ser Met Val Ser Val Gln Ala Gly Thr Lys Arg<br>        1265                      1270                    1275 | | 4261 |
| CAG TGAACTCTGA CTGTATGAGA TGTTAAATAC TTTTTAATAT TTGTTTAGAT<br>Gln<br>1280 | | 4314 |

```
ATGACATTTA TTCAAAGTTA AAAGCAAACA CTTACAGAAT TATGAAGAGG TATCTGTTTA    4374

ACATTTCCTC AGTCAAGTTC AGAGTCTTCA GAGACTTCGT AATTAAAGGA ACAGAGTGAG    4434

AGACATCATC AAGTGGAGAG AAATCATAGT TTAAACTGCA TTATAAATTT TATAACAGAA    4494

TTAAAGTAGA TTTTAAAAGA TAAAATGTGT AATTTTGTTT ATATTTTCCC ATTTGGACTG    4554

TAACTGACTG CCTTGCTAAA AGATTATAGA GTAGCAAAA AGTATTGAAA TGTTTGCATA    4614

AAGTGTCTAT AATAAAACTA AACTTTCATG TGAAAAAAAA AAAAAAAAAA AAAAA        4669
```

(2) INFORMATION FOR SEQ ID NO: 2:

(i) SEQUENCE CHARACTERISTICS:
        (A) LENGTH: 1280 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Asp Leu Glu Gly Asp Arg Asn Gly Gly Ala Lys Lys Lys Asn Phe
 1               5                  10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
        50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285
```

-continued

```
Ile Lys Lys Ala Ile Thr Ala Asn Ile Ser Ile Gly Ala Ala Phe Leu
    290                 295                 300

Leu Ile Tyr Ala Ser Tyr Ala Val Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
                355                 360                 365

Ile Asp Asn Lys Pro Ser Ile Asp Ser Tyr Ser Lys Ser Gly His Lys
370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
                515                 520                 525

Ala Gln Leu Ser Gly Gly Gln Lys Gln Arg Ile Ala Ile Ala Arg Ala
530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Phe Ala Thr Val
                580                 585                 590

Arg Asn Ala Asp Val Ile Ala Gly Phe Asp Asp Gly Val Ile Val Glu
                595                 600                 605

Lys Gly Asn His Asp Glu Leu Met Lys Glu Lys Gly Ile Tyr Phe Lys
610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln His Arg Lys Leu Ser Thr Lys Glu Ala Leu
                675                 680                 685

Asp Glu Ser Ile Pro Pro Val Ser Phe Trp Arg Ile Met Lys Leu Asn
690                 695                 700

Leu Thr Glu Trp Pro Tyr Phe Val Val Gly Val Phe Cys Ala Ile Ile
```

-continued

```
            705                 710                 715                 720
Asn Gly Gly Leu Gln Pro Ala Phe Ala Ile Ile Phe Ser Lys Ile Ile
                725                 730                 735
Gly Val Phe Thr Arg Ile Asp Asp Pro Glu Thr Lys Arg Gln Asn Ser
                740                 745                 750
Asn Leu Phe Ser Leu Leu Phe Leu Ala Leu Gly Ile Ile Ser Phe Ile
                755                 760                 765
Thr Phe Phe Leu Gln Gly Phe Thr Phe Gly Lys Ala Gly Glu Ile Leu
        770                 775                 780
Thr Lys Arg Leu Arg Tyr Met Val Phe Arg Ser Met Leu Arg Gln Asp
785                 790                 795                 800
Val Ser Trp Phe His Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
                820                 825                 830
Leu Ala Val Ile Thr Gln Asn Ile Ala Asn Leu Gly Thr Gly Ile Ile
                835                 840                 845
Ile Ser Phe Ile Tyr Gly Trp Gln Leu Thr Leu Leu Leu Leu Ala Ile
        850                 855                 860
Val Pro Ile Ile Ala Ile Ala Gly Val Val Glu Met Lys Met Phe Ala
865                 870                 875                 880
Gly Gln Ala Leu Lys Asp Lys Lys Glu Leu Glu Gly Ala Gly Lys Ile
                885                 890                 895
Ala Thr Glu Ala Ile Glu Asn Phe Arg Thr Val Val Ser Leu Thr Gln
                900                 905                 910
Glu Gln Lys Phe Glu His Met Tyr Ala Gln Ser Leu Gln Val Pro Tyr
                915                 920                 925
Arg Asn Ser Leu Arg Lys Ala His Ile Phe Gly Ile Thr Phe Ser Phe
        930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                965                 970                 975
Val Phe Ser Ala Val Val Phe Gly Ala Met Ala Val Gly Gln Val Ser
                980                 985                 990
Ser Phe Ala Pro Asp Tyr Ala Lys Ala Lys Ile Ser Ala Ala His Ile
        995                 1000                1005
Ile Met Ile Ile Glu Lys Thr Pro Leu Ile Asp Ser Tyr Ser Thr Glu
        1010                1015                1020
Gly Leu Met Pro Asn Thr Leu Glu Gly Asn Val Thr Phe Gly Glu Val
1025                1030                1035                1040
Val Phe Asn Tyr Pro Thr Arg Pro Asp Ile Pro Val Leu Gln Gly Leu
                1045                1050                1055
Ser Leu Glu Val Lys Lys Gly Gln Thr Leu Ala Leu Val Gly Ser Ser
                1060                1065                1070
Gly Cys Gly Lys Ser Thr Val Val Gln Leu Leu Glu Arg Phe Tyr Asp
        1075                1080                1085
Pro Leu Ala Gly Lys Val Leu Leu Asp Gly Lys Glu Ile Lys Arg Leu
        1090                1095                1100
Asn Val Gln Trp Leu Arg Ala His Leu Gly Ile Val Ser Gln Glu Pro
1105                1110                1115                1120
Ile Leu Phe Asp Cys Ser Ile Ala Glu Asn Ile Ala Tyr Gly Asp Asn
                1125                1130                1135
```

```
Ser Arg Val Val Ser Gln Glu Glu Ile Val Arg Ala Ala Lys Glu Ala
        1140            1145            1150

Asn Ile His Ala Phe Ile Glu Ser Leu Pro Asn Lys Tyr Ser Thr Lys
        1155            1160            1165

Val Gly Asp Lys Gly Thr Gln Leu Ser Gly Gly Gln Lys Gln Arg Ile
    1170            1175            1180

Ala Ile Ala Arg Arg Leu Val Arg Gln Pro His Ile Leu Leu Leu Asp
1185            1190            1195            1200

Glu Ala Thr Ser Ala Leu Asp Thr Glu Ser Glu Lys Val Val Gln Glu
            1205            1210            1215

Ala Leu Asp Lys Ala Arg Glu Gly Arg Thr Cys Ile Val Ile Ala His
            1220            1225            1230

Arg Leu Ser Thr Ile Gln Asn Ala Asp Leu Ile Val Val Phe Gln Asn
        1235            1240            1245

Gly Arg Val Lys Glu His Gly Thr His Gln Gln Leu Leu Ala Gln Lys
    1250            1255            1260

Gly Ile Tyr Phe Ser Met Val Ser Val Gln Ala Gly Thr Lys Arg Gln
1265            1270            1275            1280
```

METHODS AND REAGENTS FOR PREPARING AND USING IMMUNOLOGICAL AGENTS SPECIFIC FOR P-GLYCOPROTEIN

This application is a divisional of U.S. Ser. No. 09/316,167, filed May 21, 1999, now U.S. Pat. No. 6,365,357, issued Apr. 2, 2002, which is is a continuation-in-part of U.S. patent application Ser. No. 08/752,447, filed Nov. 15, 1996, now U.S. Pat. No. 5,994,088, the disclosure of which is incorporated by reference in its entirety herein.

BACKGROUND OF THE INVENTION

1. Field of the Invention

The present invention relates to uses of immunological reagents specific for a human transmembrane efflux pump protein (P-glycoprotein). Specifically, the invention relates to uses of such immunological reagents that specifically recognize P-glycoprotein that is in a biochemical conformation adopted in the presence of certain cytotoxic, lipophilic drugs that are substrates for P-glycoprotein, in the presence of cellular ATP depleting agents, and by certain mutant embodiments of Pgp. In particular, the invention provides methods of using such immunological reagents for anticancer drug screening and development.

2. Background of the Invention

Many human cancers express intrinsically or develop spontaneously resistance to several classes of anticancer drugs, each with a different structure and different mechanism of action. This phenomenon, which can be mimicked in cultured mammalian cells selected for resistance to certain plant alkaloids or antitumor antibiotics such as colchicine, vinblastine and doxorubicin (formerly known as Adriamycin), is generally referred to as multidrug resistance ("MDR"; see Roninson (ed)., 1991, *Molecular and Cellular Biology of Multidrug Resistance in Tumor Cells*, Plenum Press, N.Y., 1991; Gottesman et al., 1991, in *Biochemical Bases for Multidrug Resistance in Cancer*, Academic Press, N.Y., Chapter 11 for reviews). The MDR phenotype presents a major obstacle to successful cancer chemotherapy in human patients.

MDR frequently appears to result from decreased intracellular accumulation of anticancer drugs as a consequence of increased drug efflux related to alterations at the cellular plasma membrane. When mutant cell lines having the MDR phenotype are isolated, they are found to express an ATP-dependent non-specific molecular "pump" protein (generally known as P-glycoprotein) that is located in the plasma membrane and keeps the intracellular accumulation of an anti-cancer drug low enough to evoke the drug-resistance phenotype. This protein (which has been determined to be the gene product of the MDR1 gene in humans) facilitates active (i.e., energy-dependent) drug efflux from the cell, against a concentration gradient of (generally) lipophilic compounds, including many cytotoxic drugs.

The gene encoding P-glycoprotein (which is also known as gp170–180 and the multidrug transporter) has been cloned from cultured human cells by Roninson et al. (see U.S. Pat. No. 5,206,352, issued Apr. 27, 1993), and is generally referred to as MDR1. The protein product of the MDR1 gene, most generally known as P-glycoprotein ("Pgp"), is a 170–180 kilodalton (kDa) transmembrane protein having the aforementioned energy-dependent efflux pump activity.

Molecular analysis of the MDR1 gene indicates that Pgp consists of 1280 amino acids distributed between two homologous halves (having 43% sequence identity of amino acid residues), each half of the molecule comprising six hydrophobic transmembrane domains and an ATP binding site within a cytoplasmic loop. Only about 8% of the molecule is extracellular, and carbohydrate moieties (approximately 30 kDa) are bound to sites in this region (Chen et al., 1986, *Cell* 47: 381–387).

Expression of Pgp on the cell surface is sufficient to render cells resistant to many (but not all) cytotoxic drugs, including many anti-cancer agents. Pgp-mediated MDR appears to be an important clinical component of drug resistance in tumors of different types, and MDR1 gene expression correlates with resistance to chemotherapy in different types of cancer.

Pgp is also constitutively expressed in many normal cells and tissues (see Cordon-Cardo et all, 1990, *J. Histochem. Cytochem.* 38: 1277; and Thiebaut et al., 1987, *Proc. Natl. Acad. Sci. USA* 84: 7735 for reviews). In hematopoietic cells, Neyfakh et al. (1989, *Exp. Cancer Res.* 185: 496) have shown that certain subsets of human and murine lymphocytes efflux Rh123, a fluorescent dye that is a Pgp substrate, and this process can be blocked by small molecule inhibitors of Pgp. It has been demonstrated more recently that Pgp is expressed on the cell-surface membranes of pluripotent stem cells, NK cells, CD4- and CD8-positive T lymphocytes, and B lymphocytes (Chaudhary et al., 1992, *Blood* 80: 2735; Drach et al., 1992, *Blood* 80: 2729; Kimecki et al., 1994, *Blood* 83: 2451; Chaudhary et al., 1991, *Cell* 66: 85). Pgp expression on the cell surface membranes of different subsets of human lymphocytes has been extensively documented (Coon et al., 1991, *Human Immunol.* 32: 134; Tiirikainen et al., 1992, *Ann. Hematol.* 65: 124; Schluesener et al., 1992, *Immunopharmacology* 23: 37; Gupta et al., 1993, *J. Clin. Immunol.* 13: 289). Although recent studies suggest that Pgp plays a role in normal physiological functions of immune cells (Witkowski et al., 1994, *J. Immunol.* 153: 658; Kobayashi et al., 1994, *Biochem. Pharmacol.* 48: 1641; Raghu et al., 1996, *Exp. Hematol.* 24: 1030–1036), the physiological role of Pgp in normal immune cells has remained unclear to date.

Once the central role in MDR played by Pgp was uncovered, agents with a potential for reversing MDR phenotypes were developed that target Pgp. Several classes of drugs, including calcium channel blockers (e.g., verapamil), immunosuppresants (such as cyclosporines and steroid hormones), calmodulin inhibitors, and other compounds, were found (often fortuitously) to enhance the intracellular accumulation and cytotoxic action of Pgp-transported drugs (Ford et al., 1990, *Pharm. Rev.* 42: 155). Many of these agents were found to inhibit either drug binding or drug transport by Pgp (Akiyama et al., 1988, *Molec. Pharm.* 33: 144; Horio et al., 1988, *Proc. Natl. Acad. Sci. USA* 84: 3580). Some of these agents themselves were found to bind to and be effluxed by Pgp, suggesting that their enhancing effects on the cytotoxicity of Pgp substrates are due, at least in part, to competition for drug binding sites on this protein (Cornwell et al., 1986, *J. Bio. Chem.* 261: 7921; Tamai, 1990, *J. Biochem. Molec. Biol.* 265: 16509).

Many of these agents, however, also have strong, deleterious side effects at physiologically-achievable concentrations. These systemic side effects severely limit the clinical use of these agents as specific inhibitors of Pgp or for negative selection against Pgp-expressing tumor cells. Most of the known MDR-reversing drugs used in clinical trials have major side effects unrelated to inhibition of Pgp, such as calcium channel blockage (verapamil) or immunosuppression (cyclosporines and steroids). Similarly, targeting of cytotoxic drugs to Pgp-expressing cells is capable of compromising normal tissue function in normal cells (such as kidney, liver, colonic epithelium, etc.) that normally express Pgp. These drawbacks restrict the clinically-achievable dose of such agents and ultimately, their usefulness.

Immunological reagents also provide a means for specifically inhibiting drug efflux mediated by Pgp. Monoclonal antibodies specific for Pgp are known in the art.

Hamada et al., 1986, *Proc. Natl. Acad. Sci. USA* 83: 7785 disclose the mAbs MRK-16 and MRK-17, produced by immunizing mice with doxorubicin-resistant K-562 human leukemia cells. MRK-16 mAb was also reported to modulate vincristine and actinomycin D transport in resistant cells, and MRK-17 was shown to specifically inhibit growth of resistant cells with these drugs.

Meyers et al., 1987, *Cancer Res.* 49: 3209 disclose mAbs HYB-241 and HYB-612, which recognize an external epitope of Pgp.

O'Brien et al., 1989, *Proc. Amer. Assoc. Cancer Res.* 30:Abs 2114 disclose that mAbs HYB-241 and HYB-612 increased the accumulation of vincristine and actinomycin D in tumor cells and increased the cytotoxicity of combinations of these drugs with verapamil.

Tsuruo et al., 1989, *Jpn. J. Cancer Res.* 80: 627 reported that treatment of athymic mice that had been previously inoculated with drug resistant human ovarian cancer cells with the mAb MRK16 caused regression of established subcutaneous tumors.

Hamada et al., 1990, *Cancer Res.* 50: 3167 disclosed a recombinant chimeric antibody that combines the variable region of MRK-16 with the $F_c$ portion of a human antibody, and showed this chimeric antibody to be more effective than MRK-16 mAb in increasing cytotoxicity in vitro.

Pearson et al., 1991, *J. Natl. Cancer Inst.* 88: 1386 disclosed that MRK-16 mAb increased the in vivo toxicity of vincristine to a human MDR colon cancer cell line grown as a xenograft in nude mice. The in vitro potentiation of drug cytotoxicity by MRK-16 mAb was, however, weak relative to known chemical inhibitors of Pgp action, and was apparently limited to only two Pgp substrates (vincristine and actinomycin D), having no effect on cytotoxicity by doxorubicin.

Cinciarelli et al., 1991, *Int. J. Cancer* 47: 533 disclosed a mouse $IgG_{2a}$ mAb, termed MAb657, having cross reactivity to Pgp-expressing human MDR cells. This mAb was shown to increase the susceptibility of MDR cells to human peripheral blood lymphocyte-mediated cytotoxicity, but was not shown to have an inhibitory effect on the drug efflux activity of Pgp.

Arcesi et al., 1993, *Cancer Res.* 53: 310–317 disclosed mAb 4E3 that binds to extracellular epitopes of Pgp but does not disrupt drug efflux or potentiate MDR drug-induced cytotoxicity.

Mechetner and Roninson, U.S. Pat. No. 5,434,075, issued Jul. 18, 1995, disclose mAb UIC2, having specificity for extracellular Pgp epitopes. This antibody was also shown to effectively inhibit Pgp-mediated drug efflux in MDR cells, and to reverse the MDR phenotype in vitro thereby, for a number of structurally and functional different cytotoxic compounds and all tested chemotherapeutic drugs known to be substrates for Pgp-mediated drug efflux.

There is a need in the art to develop new Pgp inhibitors for preventing or overcoming multidrug resistance in human cancer. In developing new pharmaceuticals, it is essential to determine whether a drug candidate is a Pgp substrate and is effluxed by Pgp expressed in normal or tumor cells. This is important because, on the one hand, such drugs are expected to inhibit Pgp expression in normal cells (in the gastrointestinal tract, excretory organs like kidney, certain hematopoietic cells and the blood-brain and testicular barriers), as well as tumor cells, and to compromise normal function in such organs thereby. On the other hand, tumors derived from such Pgp-expressing tissues are frequently intrinsically multidrug resistant and therefore unaffected by chemotherapeutic intervention. Finally, in all multidrug resistant tumor cells, anticancer drugs transported by Pgp decrease intracellular drug concentration, reduce the drug's "therapeutic window" and ultimately reduce the effectiveness of chemotherapeutic treatment. Thus, there is a great need in the art for reagents and assays that permit the rapid, efficient and economical screening and development of effective Pgp inhibitors.

It has been shown that small molecules that are transported by Pgp can be used to competitively inhibit Pgp-mediated efflux of chemotherapeutic drugs that are Pgp substrates. Inhibition of cytotoxic drug efflux from tumor cells in the presence of small molecule Pgp inhibitors has been shown to increase intracellular concentrations of drug and thereby increase its cytotoxic effectiveness. Such small molecules are considered promising drug candidates for selective potentiation of the antitumor effects of several anticancer drugs, including doxorubicin, taxol, vinblastine and VP-16. For example, recent clinical trials of a (relatively) non-toxic cyclosporin analog (PSC833, Novartis Corp.) demonstrated the feasibility of using small molecule Pgp inhibitors for reversing multidrug resistance in patients with hematological malignancies. These results are being actively pursued by a variety of pharmaceutical and biotechnology companies and academic researchers. Thus, development of inexpensive and reliable tests for high throughput screening and identification of new Pgp substrates is important for the development of potent Pgp reversing agents.

At present there are two techniques available for identifying Pgp transport substrates. The first is a dye-efflux assay performed using flow cytometry and is based on competitive inhibition of Pgp-mediated efflux of fluorescent dyes such as rhodamine 123. The second is an in vitro cytotoxicity assay that uses the ability of Pgp substrates to competitively inhibit Pgp-mediated efflux of cytotoxic drugs in Pgp-expressing multidrug resistant cells. In this assay, competitive inhibition of Pgp in cells cultured in the presence of cytotoxic concentrations of Pgp-effluxed cytotoxic drugs results in increased intracellular concentration of such drugs and decreased cell growth. Both assays suffer from the disadvantage that they are laborious and time-consuming and are not suitable for high throughput screening or clinical laboratory testing. In addition, these assays are not specific for Pgp because fluorescent dyes and cytotoxic drugs are also transport substrates for related multidrug resistance transporters (such as $MRP^-$; Grant et al., 1994, *Cancer Res.* 54: 357–361)

There remains a need in the art for a rapid, reliable, efficient and inexpensive method for high throughput screening of compounds for Pgp inhibiting activity in order to develop more effective chemotherapeutic treatment of human cancer patients.

SUMMARY OF THE INVENTION

The invention also provides methods for evaluating novel cytotoxic, chemotherapeutic drugs and Pgp inhibitors. The methods of the invention are based on the development of novel immunological reagents specific for Pgp in a biochemical conformation adopted in the presence of Pgp-mediated transport substrates or ATP depleting agents. The capacity to discriminate between compounds that induce this conformation in Pgp and those that do not provides a way to identify Pgp inhibitors that can be used in high throughput screening assays. These methods can be used as screening assays based on enhanced binding of certain immunological reagents such as UIC2 mAb (A.T.C.C. Accession No. HB 11027) or its derivatives in the presence of Pgp substrates and enable rapid, reliable and cost-effective characterization of potential new Pgp-targeted drugs.

The methods of the invention comprise the steps of contacting a mammalian cell expressing Pgp with an immunological reagent such as UIC2 mAb in the presence and absence of a putative Pgp binding substrate and comparing binding of the immunological reagent in the presence of the test compound with immunological reagent binding in the absence of the test compound. In preferred embodiments, the immunological binding agent is detectably labeled. More preferably, the immunological reagent is detectably labeled with a fluorescent label, and binding affinity is detected by fluorescence activated cell sorting (FACS), immunohistochemistry and similar staining methods. In one aspect of the methods of the invention, Pgp expression levels are determined, providing the capacity to quantitatively compare results between assays. In a second aspect, enhanced binding activity of the immunological reagents provide away of determining Pgp binding capacity of the test compound. The assays of the invention thus advantageously provide information on both Pgp expression and function simultaneously.

An additional advantage of the methods of the invention is that the use of immunological reagents specific for Pgp reduces the possibility that the assay results contain contributions from related species involved in multidrug resistance, such as MRP.

Specific preferred embodiments of the present invention will become evident from the following more detailed description of certain preferred embodiments and the claims.

DESCRIPTION OF THE DRAWINGS

FIGS. 1A through 1H depict the predicted nucleic acid sequence of human Pgp (Seq. I.D. No. 1), wherein the initiation (ATG) and termination (TGA) codons, as well as codons encoding mutations at amino acid positions 433 and 1076, are underlined.

FIG. 2A illustrates flow cytometric analysis of K562/I-S9 leukemia cells incubated with phycoerythrin (PE)-conjugated mAb in the presence or absence of vinblastine.

FIGS. 5A through 5D illustrates flow cytometric analysis of mouse L cell transfectants expressing wildtype (KK-L) double mutant (MM) or single mutant (MK-H or KM-H) human Pgp incubated with PE-conjugated UIC2 (FIGS. 5A and 5C) or MRK16 (FIGS. 5B and 5D).

FIGS. 6A and 6B), or double mutant (MM; FIGS. 6C and 6D) human Pgp incubated with PE-conjugated UIC2 (FIGS. 6A and 6C) or MRK16 (FIGS. 6B and 6D) in the presence of absence of taxol, vinblastine or etoposide.

FIG. 8A or KK-H; FIG. 8B), single mutant (MK-H; FIG. 8C; or KM; FIG. 8D) or double mutant (MM; FIG. 8E) human Pgp incubated with PE-conjugated UIC2 in the presence or absence of vinblastine and the ATP depletion agents oligomycin, azide and cyanide.

FIG. 12 illustrates flow cytometric analysis of MCF7-40F P4 breast cancer cells incubated with PE-conjugated UIC2 in the presence or absence of cyclosporine, cisplatin or SN-38 as described in Example 5.

DETAILED DESCRIPTION OF THE PREFERRED EMBODIMENTS

Figure 2B:
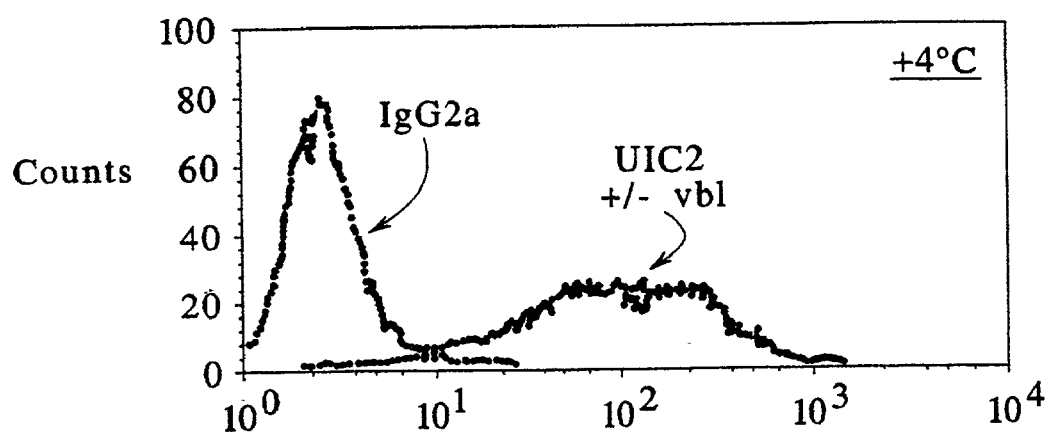
FIG. 2B illustrates flow cytometric analysis of K562/I-S9 leukemia cells incubated with PE-conjugated UIC2 mAb in the presence or absence of vinblastine at 4° C.

The present invention provides a variety of methods related to P-glycoprotein mediated multidrug resistance in mammalian, most preferably human, cells. For the purposes of the present invention, "multidrug resistance" is defined as cross-resistance to at least the following cytotoxic drugs: vinblastine, vincristine, doxorubicin, colchicine, actinomycin D, etoposide, taxol, puromycin, and gramicidin D; it will be recognized that cross-resistance to other cytotoxic drugs also falls within the meaning of multidrug resistance as it is understood by those with skill in the art. Such drugs are generally referred to herein as MDR drugs.

The methods of the invention are based in significant part on the discovery by the present inventors that the mAb UIC2, which is capable of inhibiting drug efflux from Pgp-expressing cells, specifically binds to Pgp in a particular biochemical conformation. For the purposes of this invention this biochemical conformation is functionally defined as the conformation adopted by human Pgp in the presence of Pgp substrates or ATP depleting agents, and results in enhanced binding of the mAb UIC2. Also within this definition are certain mutant forms of Pgp having disabling mutations in the nucleotide binding sites, wherein ATPase activity is disabled, as described below, in Loo and Clarke (1995, *J. Biol. Chem.* 270: 21449–21452) and in Müller et al. (1996, *J. Biol. Chem* 271: 1877–1883). For the purposes of this invention, exemplary Pgp transport substrates include a variety of lipophilic, cytotoxic natural product drugs used in cancer chemotherapy, including but not limited to Vinca alkaloids, epipodophyllotoxins, anthracyclines, etoposide, colchicine, colcemid and taxol, as well as the antibiotics monensin and actinomycin D and the interleukin cytokines. For the purposes of this invention, the term "ATP-depleting agent" is intended to include, but is not limited to, 2-deoxyglucose, cyanine, oligomycin, valinomycin and azide, as well as salts and derivatives thereof.

The invention provides methods for detecting functional P-glycoprotein expression in a mammalian cell, particularly a malignant mammalian cell and most particularly a multidrug resistant malignant mammalian cell. For the purposes of this invention, the term "functional Pgp expression" is intended to encompass the production of Pgp protein in a cell membrane, most preferably the plasma membrane, wherein the Pgp is capable of transporting an MDR drug across said membrane and against a concentration or solubility gradient. "Functional Pgp expression" is also intended to encompass Pgp protein molecules having an ATPase activity.

In the methods of the invention provided to detect functional Pgp expression in a mammalian cell, the immunological reagent is preferably provided wherein the extent and amount of specific binding of the reagent to Pgp expressed by the mammalian cell is increased in the presence of a Pgp substrate or ATP-depleting agent. For the purposes of this invention, it will be understood that the invention thus provides methods and reagents wherein specific binding of the immunological reagents is enhanced in the presence of a Pgp substrate or ATP-depleting agent, as compared with specific binding of the immunological reagent to the mammalian cell in the absence of a Pgp substrate or ATP-depleting agent. Such enhanced binding is detected using any method known to the skilled artisan, including but not limited to detection of binding of detectably-labeled embodiments of the immunological reagents of the invention, and detection of specific binding of the immunological reagents of the invention using a detectably-labeled immunological reagent that is specific for the immunological reagents of the invention (e.g., in a "sandwich-type" immunoassay). Alternatively, and preferably, the methods of the invention include conventional cell separation methods and techniques, including but not limited to fluorescence activated cell sorting techniques. In other embodiments, the methods of the invention are provided wherein the immunological reagents of the invention are recognized by detectably-labeled second immunological reagents which specifically recognize the immunological reagents of the invention (for example, based on isotypic, allotypic or species-specific antibodies or antisera).

For the purposes of this invention, the term "immunological reagents" is intended to encompass antisera and antibodies, particularly monoclonal antibodies, as well as fragments thereof (including F(ab), F(ab)$_2$, F(ab)' and F$_v$ fragments). Also included in the definition of immunological reagent are chimeric antibodies, humanized antibodies, and recombinantly-produced antibodies and fragments thereof. Immunological methods used in conjunction with the reagents of the invention include direct and indirect (for example, sandwich-type) labeling techniques, immunoaffinity columns, immunomagnetic beads, fluorescence activated cell sorting (FACS), enzyme-linked immunosorbent assays (ELISA), and radioimmune assay (RIA). For use in these assays, the Pgp-specific immunological reagents can be labeled, using fluorescence, antigenic, radioisotopic or biotin labels, among others, or a labeled secondary immunological detection reagent can be used to detect binding of the Pgp-specific immunological reagents (i.e., in secondary antibody (sandwich) assays).

The UIC2 mAb is one example of the immunological reagents of the invention. This mAb is directed to an epitope in an extracellular domain of human Pgp, and was made by immunizing mice with mouse cells that have been made MDR by transfection with an isolated human MDR1-encoding cDNA (see U.S. Ser. No. 07/626,836, incorporated by reference). Briefly, immunogenic cells (preferably transfected syngeneic mouse fibroblasts) were used to immunize BALB/c mice (e.g., transfected BALB/c mouse 3T3 fibroblasts). MDR derivatives of mouse BALB/c 3T3 fibroblasts were generated with human MDR1-encoding DNA, and cells selected and grown in cytotoxic concentrations of an MDR drug. Once produced, MDR fibroblasts were selected in which the transfected MDR1 gene had been amplified, by consecutive steps of selection in progressively higher concentrations of an MDR drug. This produced highly multidrug resistant cells that expressed large amounts of Pgp inserted into the cellular plasma membrane resulting in high levels of MDR (e.g., BALB/c 3T3-1000 cells are resistant to vinblastine at a concentration of 1000 ng/mL).

Such cells were used to immunize syngeneic mice. Appropriate numbers of cells were injected subcutaneously (s.c.) or intraperitoneally (i.p.) by art-recognized immunization protocols (see U.S. Pat. No. 5,434,075, issued Jul. 18, 1995, incorporated in their entirety herein). Typically, $10^5$ to $10^8$ transfected cells were injected 5 or 6 times at two week intervals, and a final boosting was done with, for example, $10^6$ cells subcutaneously and/or intravenously. At an appropriate time after the booster injection, typically 3 to 5 days thereafter, the spleen was harvested from a hyperimmune mouse, and hybridomas generated by standard procedures (see, e.g., Kearney et al., 1979, *J. Immunol.* 123: 1548) using human myeloma cells, for example, P3-X63-Ag 8.653 (A.T.C.C., Rockville, Md.).

Extracellular fluids from individual hybridoma cultures were screened for specific mAb production by conventional methods, such as by indirect immunofluorescence using non-Pgp expressing control cells (e.g. non-transfected fibroblasts) and human Pgp-expressing (e.g. BALB/c 3T3-1000) cells affixed to glass slides, and FITC-labeled goat anti-mouse polyvalent immunoglobulins (Sigma Chemical Co., St. Louis, Mo.) as the secondary, reporter antibody. The particular screening method used was not critical provided that it was capable of detecting anti-human MDR1 Pgp mAb. It is important, however, that cells are not permeabilized and fixed during screening (i.e., they are living cells), so that only antibodies reactive with extracellular protein domains are detected.

A stable hybridoma producing the UIC2 mAb was established by conventional methods, such as by consecutive rounds of subcloning by, e.g., end-point dilution, and screening the culture medium for monoclonal antibodies. The hybridoma was propagated by, for example, growth in ascites fluid in vivo in syngeneic animals, and the secreted antibody isolated and purified from ascites fluid by affinity chromatography with a Sepharose-Protein A matrix specific for an IgG isotype. It will be understood that other procedures for immunoglobulin purification well known in the art are also useful for producing hybridomas that express Pgp-specific antibodies.

Alternative methods for producing mAbs are known in the art (as described in U.S. Pat. No. 5,434,075, issued Jul. 18, 1995, incorporated in its entirety herein).

mAbs produced by the UIC2 hybridoma, as well as fragments and recombinant derivatives thereof, were characterized as to immunoglobulin isotype, reactivity with different Pgp-expressing cell lines and binding to Pgp in MDR cells using art-recognized techniques (see U.S. Pat. No. 5,434,075, issued Jul. 18, 1995, incorporated by reference). As provided herein, preferred mAbs of the invention specifically bind to Pgp in a biochemical conformation adopted in the presence of Pgp-mediated transport substrates or ATP depleting agents, or in certain Pgp mutants as described herein.

The effect of anti-Pgp mAbs, fragments or recombinant derivatives thereof on Pgp function was assessed by studying the efflux of fluorescent or radioactively labeled drugs from MDR cells in the presence of absence of mAb. The effects of antibody preparations on drug cytotoxicity were assessed by incubating suspensions of MDR and control cells with the antibody preparation, then testing for cell growth inhibition in the absence and presence of an anticancer drug such as one of the Vinca alkaloids. Such assays are by definition preferred, as the mAbs of the invention are intentionally provided to be specific for substrate-bound Pgp.

Fragments of the UIC2 mAb that maintain the antigenic specificity of the complete antibody are derived by enzymatic, chemical or genetic engineering techniques (for example, partial digestion with proteolytic enzymes such as papain, pepsin or trypsin; papain digestion produces two Fab fragments and one $F_c$ fragment, while pepsin cleavage releases $F(ab)_2$ (two antigen-binding domains bound together) fragments). mAb fragments lacking the constant ($F_c$) portion are advantageous over the complete antibody for in vivo applications, as such fragments are likely to possess improved tissue permeability. Furthermore, many cells and tissues in the body express receptors capable of binding to the $F_c$ portion of antibodies, resulting in undesirable non-specific binding of the complete antibody.

The methods of the invention are not intended to be limited in scope to immunological reagents comprising the UIC2 mAb and hybridomas producing this mAb. The invention provides a variety of methods, all related to specific binding of mAbs to Pgp in a biochemical conformation adopted in the presence of Pgp-mediated transport substrates or ATP depleting agents. The UIC2 mAb is provided solely as one illustrative example of an mAb that specifically binds to Pgp and mutants thereof having such a biochemical conformation.

The Examples which follow are illustrative of specific embodiments of the invention, and various uses thereof. They set forth for explanatory purposes only, and are not to be taken as limiting the invention.

EXAMPLE 1

1. Cell Lines, Monoclonal Antibodies, and Reagents

MRK-16 mAb ($IgG_{2a}$) was obtained from Dr. T. Tsuruo, University of Tokyo, Japan. UIC2 was produced from UIC2 and UIC2/A hybridomas as described in U.S. Pat. No. 5,434,075, issued Jul. 18, 1995.

All mAb samples were at least 95% pure according to SDS-PAGE. Concentrations of the mAb were determined by the quantitative mouse Ig radial immunodiffusion kit (ICN, Costa Mesa, Calif.). When necessary, mAb's were further concentrated and dialyzed against phosphate-buffered saline (PBS) or Dulbecco modified Eagle's medium (DMEM). mAbs were conjugated with R-phycoerythrin (PE) or fluorescein isothiocyanate (FITC) at 1:1 (PE) and 1:4 (FITC) mAb:label and purified using standard techniques (Maino et al., 1995, *Cytometry* 20: 127–133). $IgG_2$-PE conjugates were purchased from Becton-Dickinson Immunocytometry Systems (BDIS, San Jose, Calif.) and used as a negative isotype control for nonspecific staining.

The K562/Inf cell line was derived by infection of human K562 leukemia cells with a recombinant retrovirus pLMDR1L6 carrying human MDR1 cDNA (Choi et al., 1991, *Proc. Natl. Acad. Sci. USA* 88: 7386–7390), and subsequently subcloned without cytotoxic selection (e.g., by FACS sorting based on Pgp-specific immunostaining or Pgp-mediated efflux of fluorescent dyes). Clones expressing relatively high levels of Pgp were selected by repeated selection of Pgp-positive clones by FACS after clonal expansion. Clone K562/I-S9 is one such FACS-selected clone (produced as described in Weisberg et al., 1996, *J. Exp. Med.* 183: 2699–2704).

LMtk⁻ cells transformed with wildtype and mutant forms of P-glycoprotein were prepared according to Morse (1996, Doctoral Dissertation, Department of Genetics, University of Illinois at Chicago, incorporated by reference herein). MDR1 cDNA-comprising constructs encoding wildtype (KK), single mutant (KM, MK) and double mutant (MM) forms of P-glycoprotein were prepared as described in Morse, wherein the mutant forms have a lysine→to—methionine mutation within either (single mutant) or both (double mutant) of the consensus ATP binding sites in the amino- and carboxyl-terminal halves of P-glycoprotein, introduced at amino acid positions 433 and 1076 by site-directed mutagenesis techniques (see Kramer et al., 1984, *Nucleic Acids Res.* 12: 9441–9456; Carter et al., 1985, *Nucleic Acids Res.* 13: 4431–4443). Each of these constructs further comprises the bacterial neomycin-resistance gene (neo), fused to the MDR1 gene via an overlapping translation termination/initiation codon (ATGA). As a consequence, MDR1 and neo are expressed in mammalian cells in a bicistronic messenger RNA. The MDR1-encoding portions of these constructs are shown in Seq. I.D. No. 1. These sequences, cloned into the mammalian expression vector expression vector pUCFVX were introduced into LMtk⁻ cells by calcium phosphate coprecipitation or electroporation (see Sambrook et al., ibid.) and transfectants selected in G418 (Grand Island Biological Co. (GIBCO), Long Island, N.Y.)-containing media. Clonal populations of Pgp wildtype or mutant-expressing cells expressing approximately equal amounts of Pgp at the cell surface were selected by FACS using fluorescently labeled mAb MRK16 and were then expanded under G418 selection.

All chemotherapeutic drugs were purchased from Sigma Chemical Co. (St. Louis, Mo.), diluted in water, DMSO or alcohol, aliquoted and stored at +4° C. for 10–14 days or at 20° C. until use.

2. Preparation of Anti-Pgp Monoclonal Antibodies

Monoclonal antibodies specific for human P-glycoprotein were prepared as disclosed in co-owned and co-pending U.S. patent application Ser. No. 07/854,881, filed Mar. 20, 1992, now U.S. Pat. No. 5,434,075, issued Jul. 18, 1995, and Ser. No. 08/032,056, filed Mar. 16, 1993, each of which are incorporated in its entirety herein.

Briefly, mouse fibroblast BALB/c 3T3 cells expressing the MDR1 gene encoding P-glycoprotein (Pgp) were derived by transfecting fibroblasts with isolated human MDR1 cDNA in a eukaryotic expression vector pUCFVXMDR1(Choi et al., 1988, *Cell* 53: 519–529), isolating multidrug-resistant cells after cytotoxic selection in 20 ng/mL of vinblastine, and subsequently amplifying the transfected gene by consecutive steps of selection in 250 ng/mL, 500 ng/mL and 1000 ng/mL of vinblastine. The resultant multidrug-resistant fibroblasts were termed BALBlc 3T3-250, BALB/c 3T3-500 and BALBlc 3T3-1000, respectively.

BALB/c mice were immunized with $1-2 \times 10^7$ of BALB/c 3T3-1000 cells, injected subcutaneously (s.c.) and/or intraperitoneally (i.p.) six times at two-week intervals. The final immunogenic boost was done with $2 \times 10^7$ cells i.p., and $5 \times 10^6$ cells administered intravenously (i.v.). Four days after the last administration of fibroblasts, the spleen from one animal was removed, and hybridomas generated by art-recognized techniques using the human myeloma cell line P3-X63-Ag8.653 (A.T.C.C. Accession No. CRL-1580).

Tissue culture supernatant fluids from individual hybridomas were screened for monoclonal antibody (mAb) production by indirect immunofluorescence labeling of live BALB/c 3T3 and BALB/c 3T3-1000 cells attached to glass slides. Fluorescein isothiocyanate (FITC)-labeled goat anti-mouse polyvalent immunoglobulins (obtained from Sigma Chemical Co., St. Louis, Mo.) were used as a secondary antibody reagent at 1:100 dilution. Of 556 tested hybridomas, mAb produced by only two hybridomas reacted with BALB/c 3T3-1000 cells, and of these two only one hybridoma (termed UIC2) produced an antibody reactive with BALB/c 3T3-1000 cells, but not with control BALB/c 3T3 cells.

A stable hybridoma line secreting UIC2 mAb was established by three consecutive rounds of subcloning by end-point dilution and screening of the supernatant fluids, as described in co-owned and co-pending U.S. patent application Ser. No. 07/854,881, filed Mar. 20, 1992, now U.S. Pat. No. 5,434,075, issued Jul. 18, 1995, and Ser. No. 08/032,056, filed Mar. 16, 1993, each of which are incorporated in its entirety herein.

The UIC2 hybridoma was propagated as ascites in syngeneic BALB/c mice, and the immunoglobulin was purified from ascites fluid by Sepharose-Protein A (Bio-Rad, Richmond, Calif.) affinity chromatography. UIC2 mAb, tested by SDS-PAGE, was at least 95% pure IgG. The UIC2 hybridoma is on deposit in the American Type Culture Collection, 10801 University Boulevard, Manassas, Va. U.S.A. 20110-2209 (Accession No. HB11027) and is available to the public.

Application of Ouchterlony and immunoblotting tests using a standard set of anti-mouse Ig antibodies revealed that the UIC2 mAb belongs to the $IgG_{2a}$ subclass.

UIC2 mAb was shown to induce complement-mediated cytotoxicity using Low-Tox-M rabbit complement (Cedarland Labs, Homby, Ontario) on BALB/c, BALB/c 3T3-1000, CEM/VLB$_{100}$, K562 and K562/Inf cell lines.

3. Fluorescence Activated Cell Sorting/Flow Cytometry Analysis

Cells were analyzed by FACSort (BDIS) equipped with an argon laser (Cyonics) tuned to 488 nm, using 4 parameters (forward scatter, side scatter, FL1 for FITC, FL2 for PE conjugates and FL3 for propidium iodide); dead cells were excluded on the basis of forward and side scatter and PI (FL3) staining. The FACS data were analyzed by the Lysis II or CellQuest computer programs.

4. ATP Depletion Experiments

Cells were depleted of intracellular ATP by incubation with oligomycin, azide or cyanide at various concentrations under conditions described in Section 3 above. Intracellular ATP was measured using the Bioluminescent Somatic Cell Assay kit (Sigma, St. Louis, Mo.), whereby the amount of ATP in cell lysates is proportional to light emitted by firefly luciferase. Intracellular ATP was expressed relative to the amount present in cells treated with PBS instead of ATP depleting agents. After incubation of cell lysates with the components of the assay kit, 0.1 mL of the reaction solution was assayed spectrophotometrically over a wavelength range of 390–622 nm using an AutoLumat LB953 Universal Luminometer (EG&G Berthold, Vildbad, Germany). All measurements were performed at 8° C. in 12×75 mm polystyrene cuvettes (Analytical Luminescence Lab, San Diego, Calif.).

EXAMPLE 2 mAb UIC2 Reactivity is Increased in the Presence of Pgp-Transported Compounds

Flow cytometry was used to analyze the reactivity of phycoerythrin (PE)-conjugated mAbs UIC2 and MRK16 with Pgp-expressing cells in the presence of different drugs. The range of optimal drug concentrations for these experiments (1–5 mg/mL) was determined by a series of preliminary titration experiments.

Figure 3A:
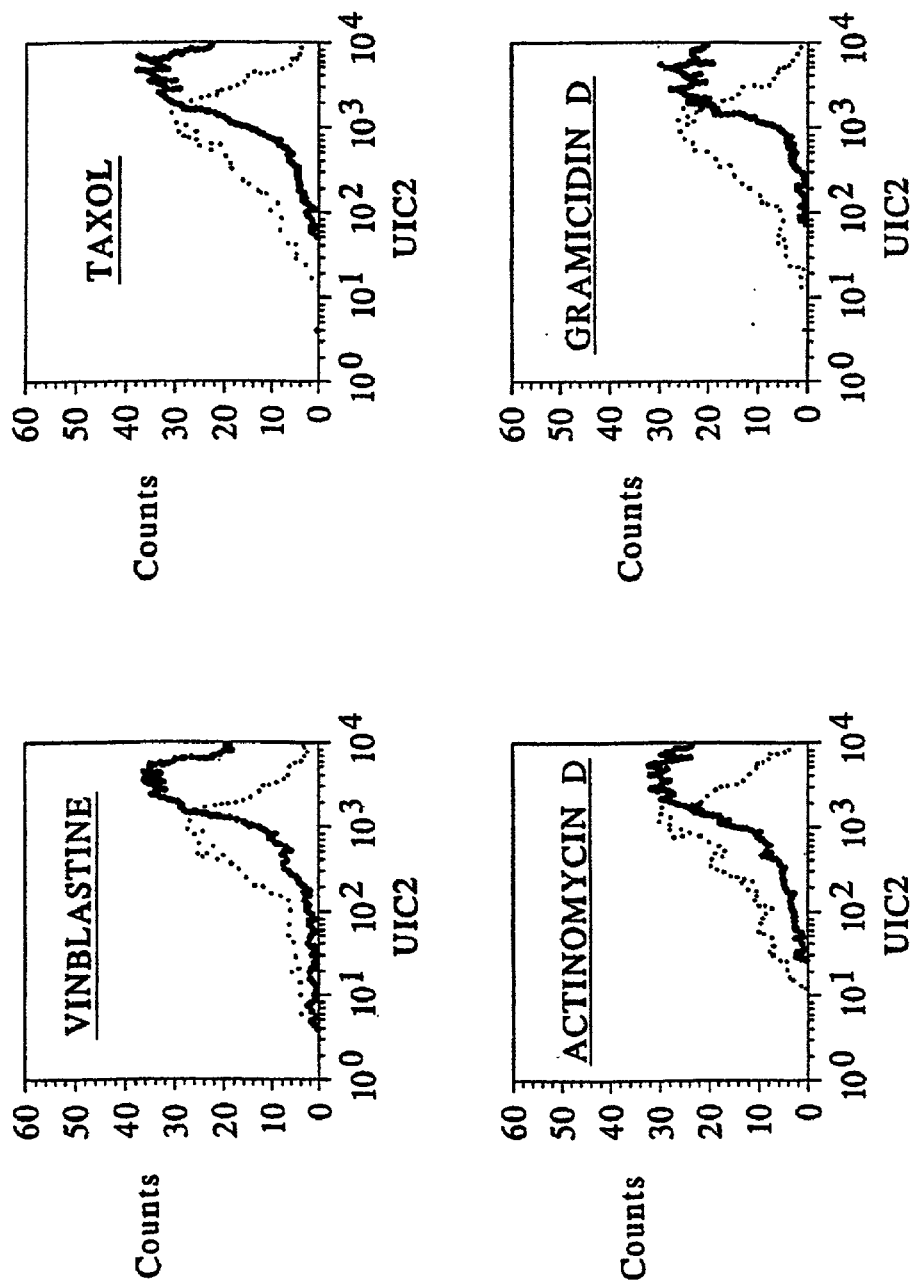
FIGS. 3A through 3D illustrate flow cytometric analysis of K562/i-S9 leukemia cells incubated with PE-conjugated UIC2 mAb (FIGS. 3A and 3B) or MRK 16 mAb (FIGS. 3C and 3D) in the presence or absence of different cytotoxic drugs.
Figure 3B:
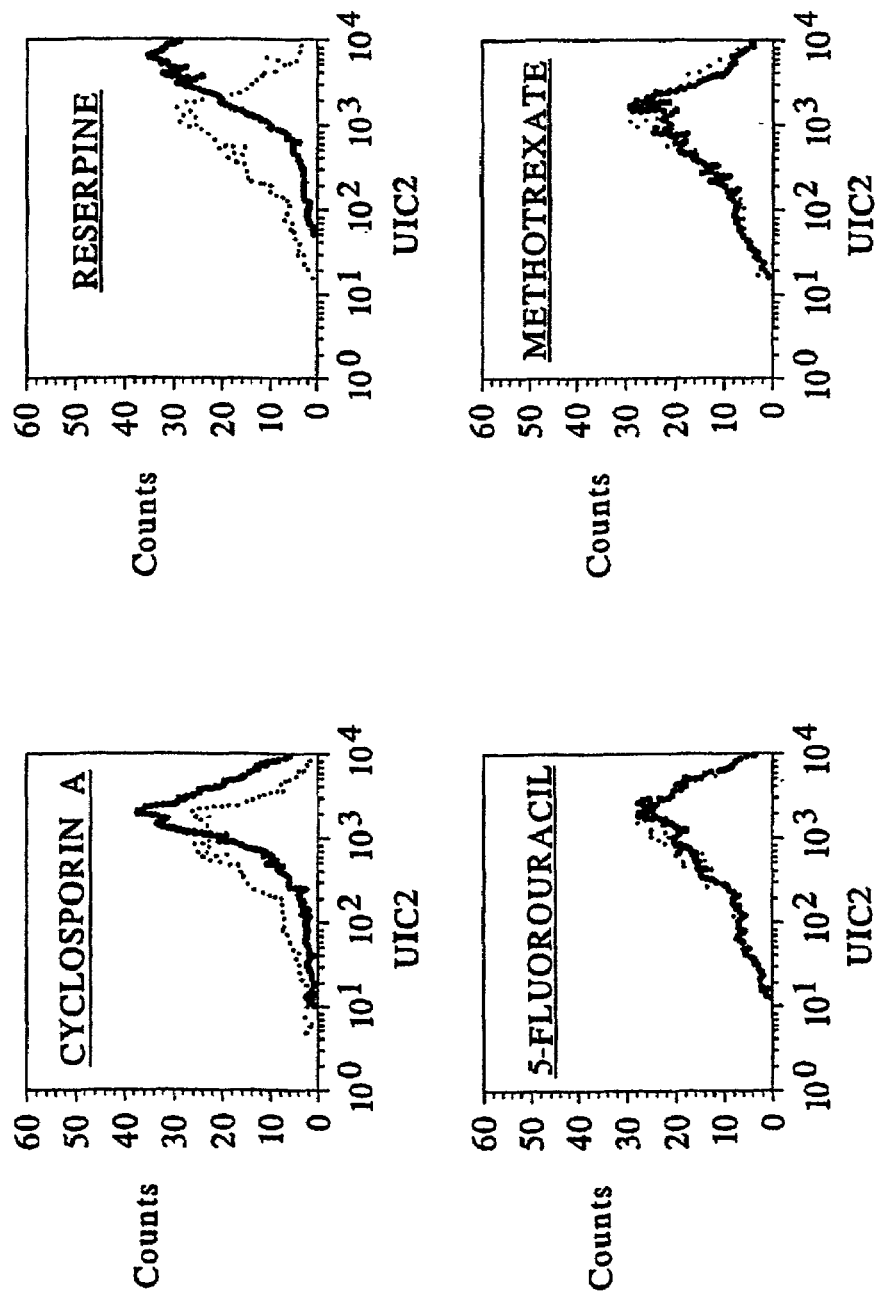
Figure 3C:
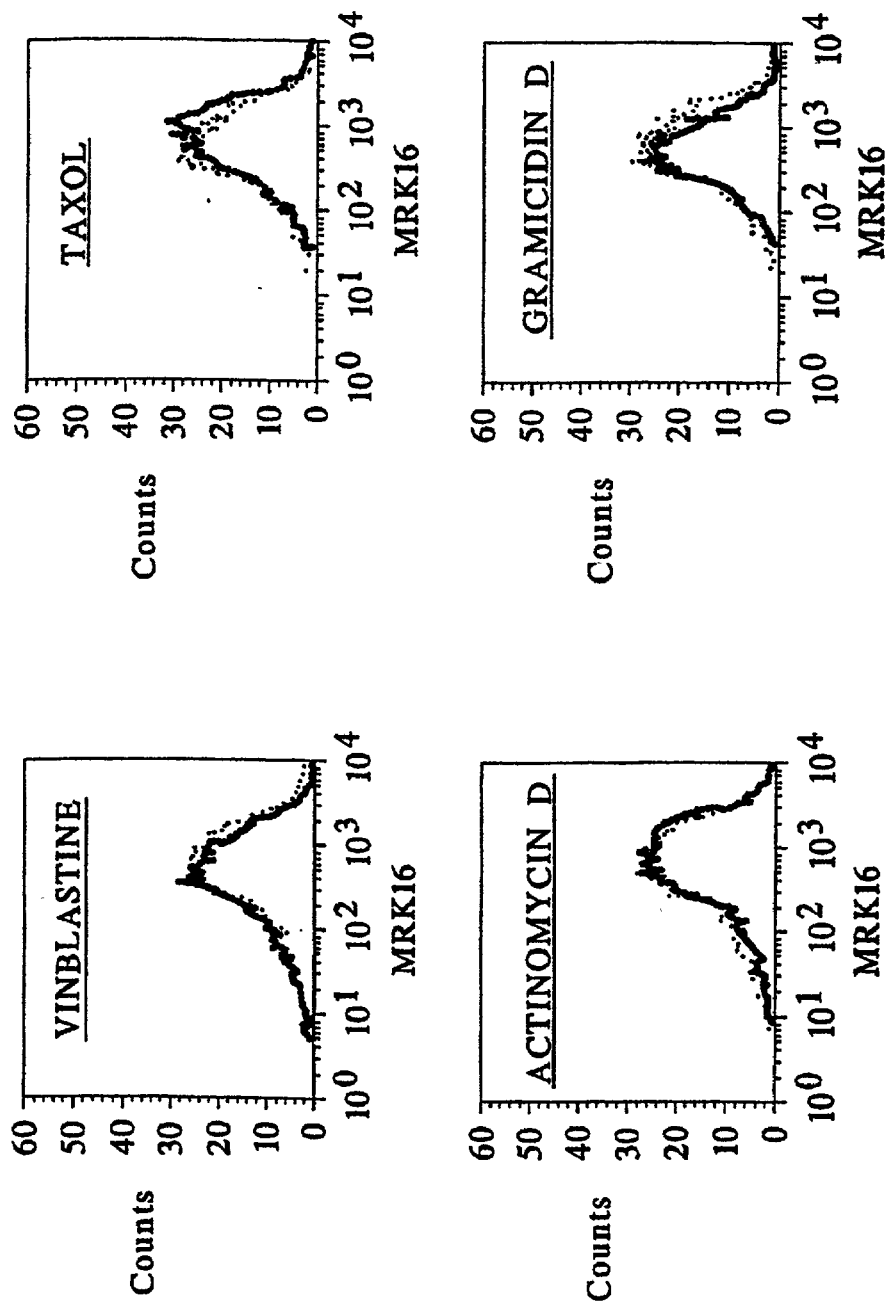
Figure 3D:
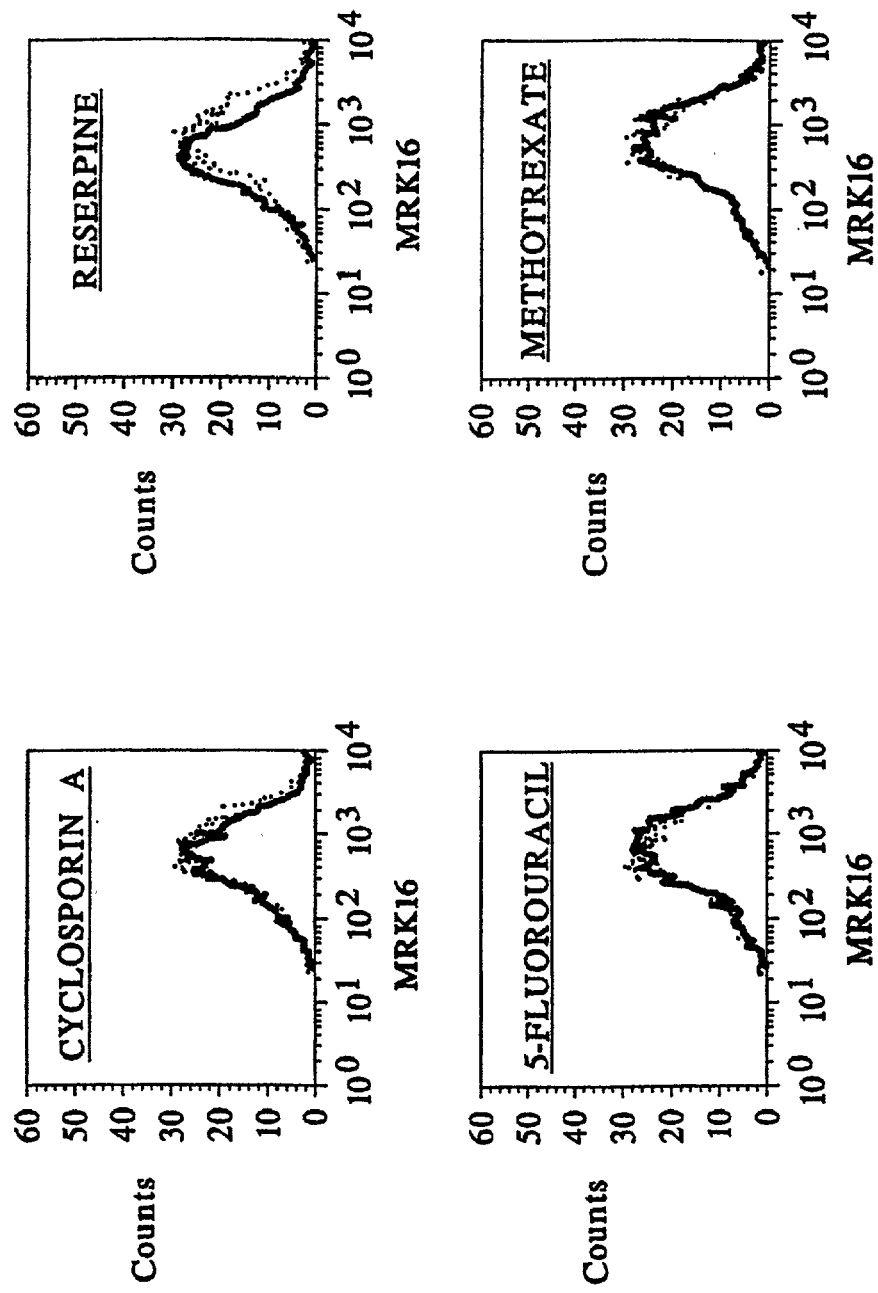
Figure 4:
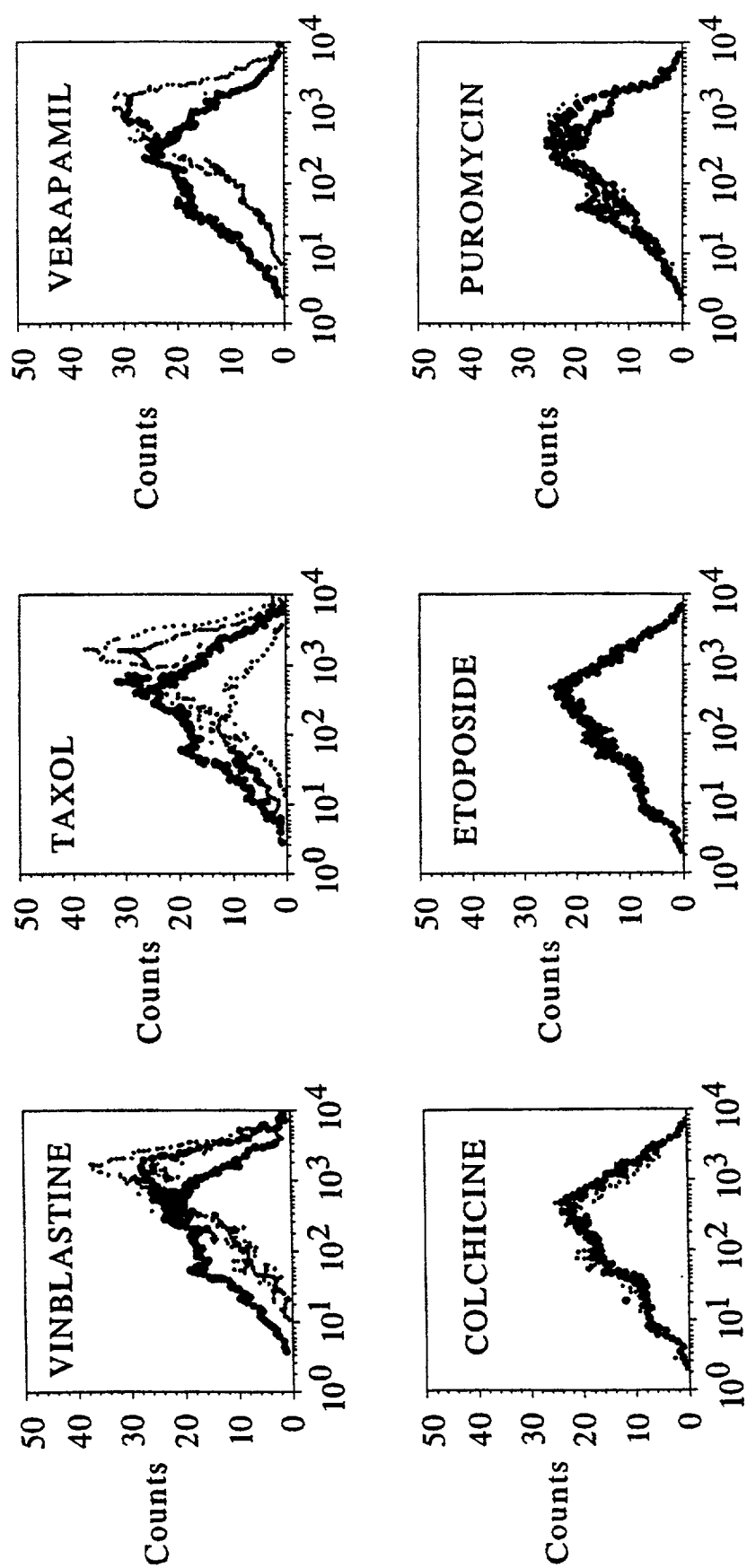
FIG. 4 illustrates flow cytometric analysis of K562/i-S9 leukemia cells incubated with PE-conjugated UIC2 mAb in the presence of increasing concentrations of vinblastine (1–625 µM), taxol (0.96–600 µM), verapamil (1.8–1125 µM), colchicine (2–1250 µM), etoposide (1.36–850 µM) and puromycin (1.72–1075 µM).

FIG. 2A illustrates the results obtained with K562/I-S9 leukemia cell line, which was selected to express Pgp by infecting K562 cells with a MDR1-transducing recombinant retrovirus and subsequent flow cytometric selection based on MRK16 antibody staining. Cells were treated in the presence or absence of 25 μM vinblastine and contacted with PE-conjugates mAbs UIC2, MRK16, IgG2a (a negative isotype control) and anti-CD54 (a positive control mAb against a cell surface marker of K562 cells). UIC2 reactivity of this cell line was increased in the presence of the Pgp-transported drug vinblastine, as seen by the rightwards shift in the flow cytometric profile at increasing drug concentrations. This profile shift was not seen with either the positive or negative control mAbs and was not seen with the Pgp-specific mAb MRK16. A similar pattern of mAb binding was observed with FITC-conjugates mAbs and in experiments performed with unlabeled mAbs detected using labeled secondary antibody (sandwich) techniques. In addition, increased UIC2 reactivity was only observed when cells were incubated with drugs and antibody at 37° C., but did not appear when incubations were performed at 4° C. (FIG. 2B), suggesting that enhanced UIC2 binding in the presence of certain Pgp substrates requires the cells to be metabolically active A variety of MDR drugs and competitive inhibitors of Pgp were tested to determine whether these compounds could induce the FACS profile shift observed with UIC2 binding in the presence of vinblastine. The tested compounds included vinblastine, taxol, actinomycin D, gramicidin D, cyclosporine A, reserpine, 5-fluorouracil and methotrexate. The results of these experiments are shown in FIG. 3A for binding of PE-UIC2 mAb and in FIG. 3B for binding of MRK16 mAb. In these experiments, a rightwards shift in the flow cytometric profile of cells contacted with PE-UIC2 mAb was observed for cells treated with vinblastine, taxol, actinomycin D, gramicidin D cyclosporine A and reserpine. No FACS profile shift was observed in cells treated with 5-fluorouracil or methotrexate, supporting the conclusion that shifting was Pgp specific and was specifically induced with Pgp substrates (since neither 5-fluorouracil or methotrexate is (typically) a Pgp substrate). In contrast, and consistent with the earlier results disclosed above, no change in the flow cytometry profile of cells contacted with MRK16 mAb was observed in cells treated with any of the tested drugs. Stimulation of UIC2 reactivity by these compounds was dose-dependent, for some compounds, while for others no shift was observed at any concentration tested (as illustrated in FIG. 4).

Increased UIC2 reactivity in the presence of Pgp substrates was also observed with other Pgp-expressing cells and cell lines, including PA317 cells expressing Pgp via an MDR1-encoding retrovirus (Choi et al, ibid.), NIH 3T3 cells, KB-3-1, VSV1 and GSV1 cells transfected with MDR1 cDNA (Choi et al., 1988, *Cell* 53: 519–529), Pgp-positive leukemia/lymphoma and tumor samples and normal B- and T-lymphocyte subpopulations and hematopoietic stem cells expressing Pgp (Chaudhary et al., 1992, *Blood* ibid.; Chaudhary et al., 1992, *Cell* ibid.). The concentrations of Pgp substrates producing maximal stimulation of UIC2 reactivity differed slightly for different cell lines and appeared to correlate with the levels of Pgp expressed on the corresponding cell lines.

A summary of these results are shown in Table I.

TABLE I

|  | UIC2 | MRK16 |
|---|---|---|
| MDR Drugs |  |  |
| taxol | + | − |
| vinblastine | + | − |
| reserpine | + | − |
| verapamil | + | − |
| gramicidin | + | − |
| cyclosporine | + | − |
| vincristine | + | − |
| actinomycin D | + | − |
| colchicine* | − | − |
| etoposide* | − | − |
| puromycin | − | − |
| Non-MDR Drugs |  |  |
| 5-fluorouracil | − | − |
| cisplatin | − | − |
| carboplatin | − | − |
| methotrexate | − | − |
| azidothymidine | − | − |
| cyclophosphamide | − | − |

*weak Pgp substrate

EXAMPLE 3

Mutations at Pgp Nucleotide-Binding Sites Alter UIC2 Reactivity

The ability of Pgp transport substrates to increase UIC2 reactivity as described in Example 2 suggested that mAb UIC2 reacts more strongly with Pgp having a conformation associated with functioning (i.e., drug-transporting) Pgp. To investigate the relationship between Pgp function and UIC2 reactivity, nucleotide-binding site mutants of Pgp were used. As described in Example 1, Pgp was mutagenized at highly conserved lysine residues (positions 433 and 1076) in the N-terminal and C-terminal nucleotide-binding sites of the human Pgp. These lysine residues were substituted with methionine residues (i.e., lysine-to-methionine (K→M) substitutions), and the resulting proteins were designated KK (wild-type Pgp), MM (double mutant), KM and MK (C-terminal and N-terminal single mutants, respectively). Analysis of immunoprecipitated Pgps showed that nucleotide binding, as measured by specific photolabeling with $^{32}$P-8-azido-ATP, was decreased in the single mutants (KM and MK) and undetectable in MM (as disclosed in Müller et al., 1996, *J. Biol. Chem.* 271: 1877–1883). In addition, all three mutants (MM, KM and MK) lost detectable ATPase activity (see Müller et al., ibid.). The double mutant, MM, also lost the ability to confer drug resistance to all tested MDR drugs (including vinblastine and vincristine). KM and MK mutant expressing cells, however, showed a 2–3 fold greater resistance to vinblastine than control cells not expressing Pgp, and accumulated 3–4 times more vinblastine than wildtype (KK)—expressing cells with the same level of vinblastine resistance. Vinblastine resistance conferred by KK, KM and MK Pgps was equally sensitive to inhibition with mAb UIC2.

For UIC2 shift experiments, two sets of murine Lmtk− transfectants were used, matched to express very similar levels of the wild-type or mutant human MDR1 Pgps. The first set includes cell lines designated KK-L (wild-type) and MM (double mutant) (FIGS. 5A through 5D and 6A through 6D). The second set, expressing about five times as much Pgp as the first set, includes cell lines KK-H (wild type), KM-H and MK-H (single mutants) (FIGS. 7A through 7F). The relative levels of Pgp expression were established on the basis of indirect immunofluorescence with PE-conjugated MRK16 (see Morse, 1996, ibid.).

FIGS. 5A and 5B show a comparison between flow cytometric analysis of KK-L and MM expressing cells contacted with UIC2 (FIG. 5A) and MRK16 (FIG. 5B). Similarly, FIGS. 5C and 5D show a comparison between flow cytometric analysis of KK-H, MK-H and KM-H expressing cells contacted with UIC2 (FIG. 5C) and MRK16 (FIG. 5D). The flow cytometric pattern of all of these cells was the same when assayed using the MRK16 mAb (see FIGS. 5B and 5D). In contrast to the results obtained using mAb MRK16, UIC2 mAb showed a strikingly different pattern of reactivity with cell lines transfected with mutant Pgps. UIC2 reacted much more strongly with the MM double mutant than with the wild-type Pgp on KK-L cells (compare in FIG. 5A). Similarly, UIC2 binding in single mutant KM-H was equivalent to wildtype binding (KK-H), while the extent of UIC2 binding to the MK-H single mutant was diminished.

Figure 6A:
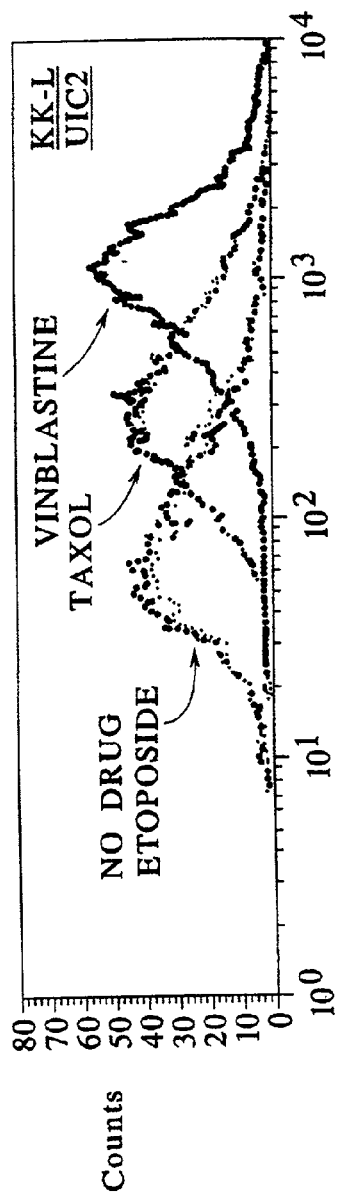
FIGS. 6A through 6D illustrates flow cytometric analysis of mouse L cell transfectants expressing wildtype (KK-L.
Figure 6B:
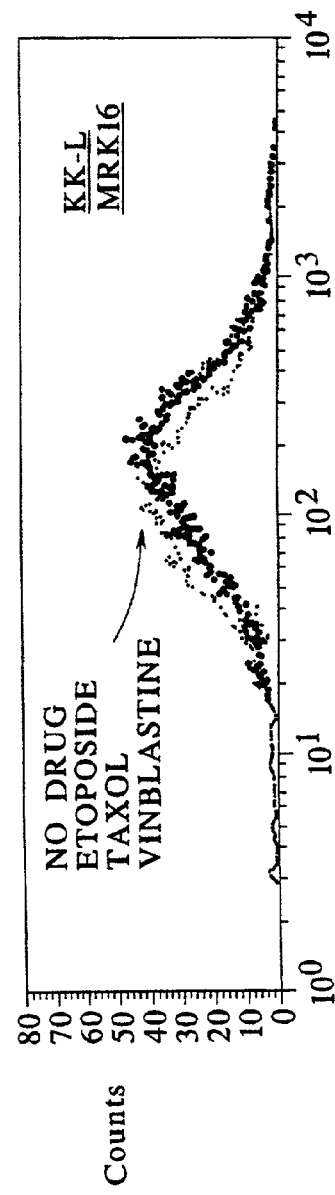
Figure 6C:
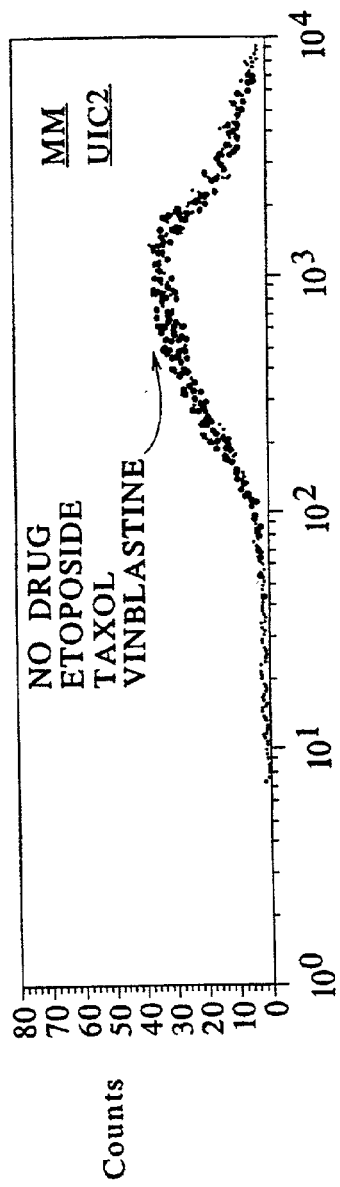
Figure 6D:
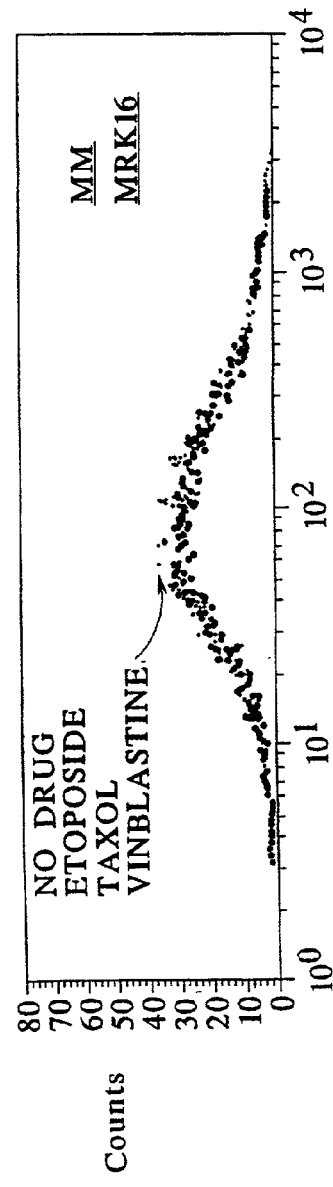
Figure 7A:
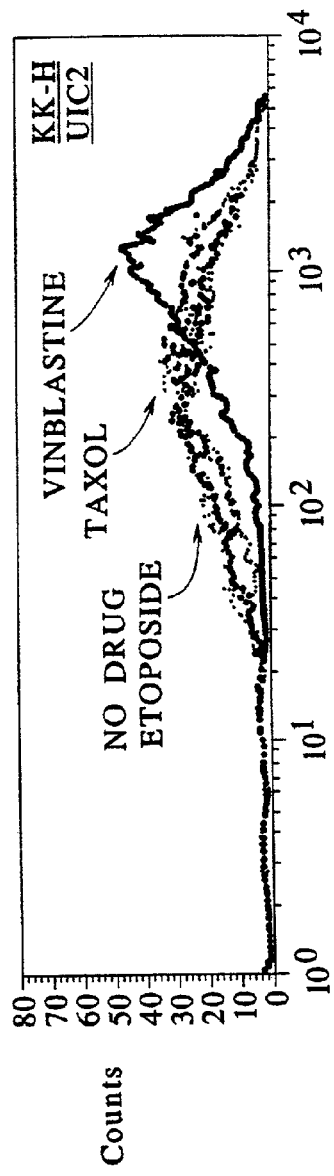
FIGS. 7A through 7F illustrate flow cytometric analysis of mouse L cell transfectants expressing wildtype (KK-H) or single mutant (KM-H and MK-H) human Pgp incubated with PE-UIC2 (FIGS. 7A, 7C and 7E) or PE-MRK16 (FIGS. 7B, 7D and 7F) in the presence or absence of vinblastine, taxol or etoposide.
Figure 7B:
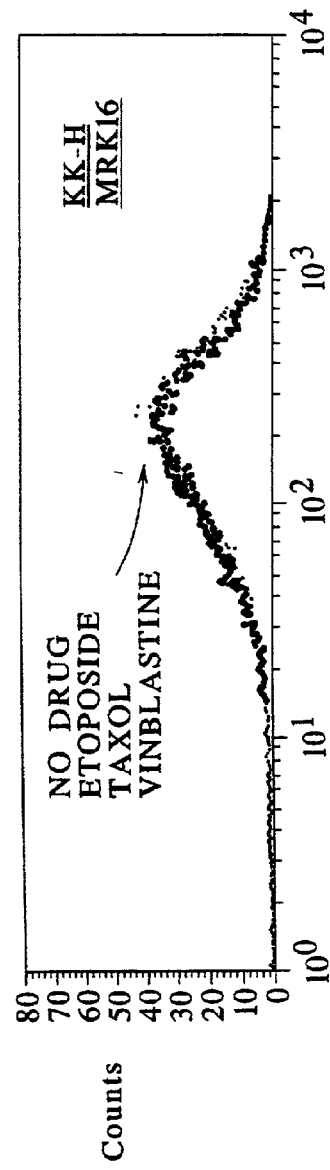
Figure 7C:
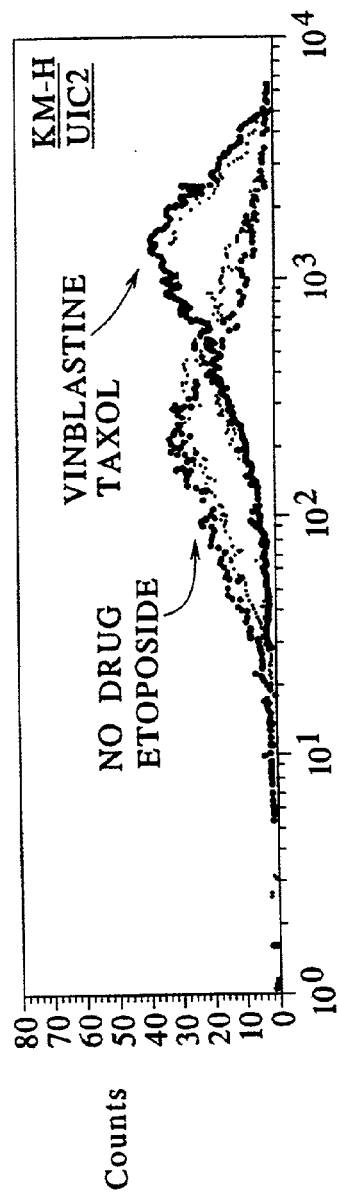
Figure 7D:
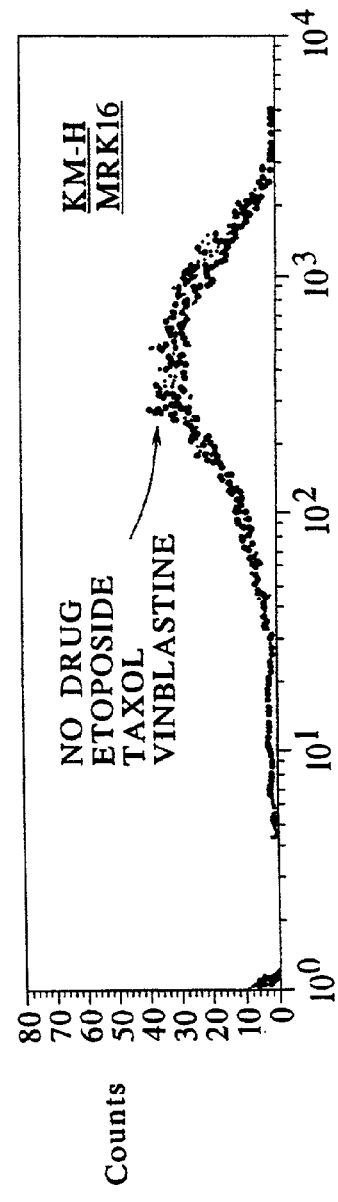
Figure 7E:
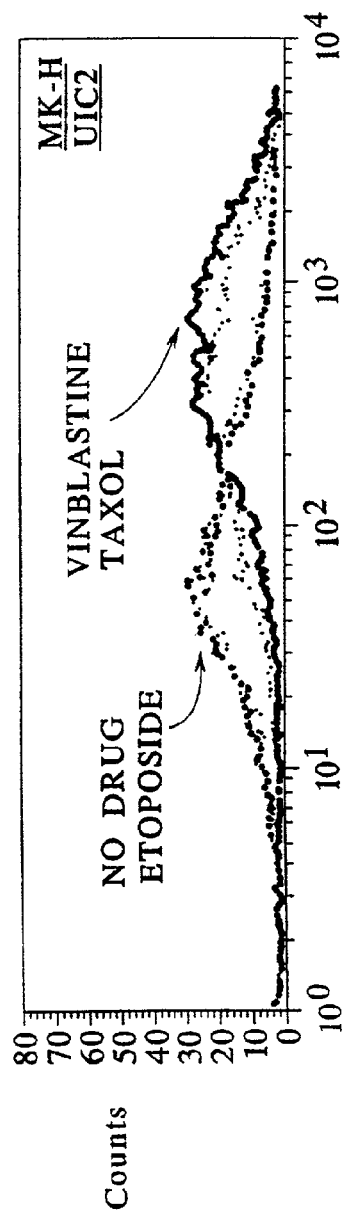
Figure 7F:
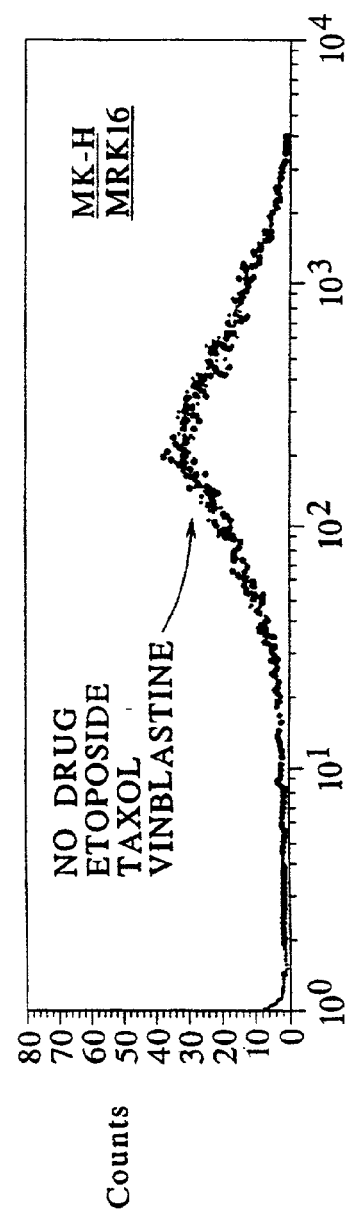

UIC2 mAb binding was compared to MRK16 binding in these cells in the presence or absence of different MDR drugs. These results are shown in FIGS. 6A through 6D. No rightwards shift in the flow cytometric profile was observed in any of the cell lines assayed using MRK16 mAb. In contrast, the wildtype KK-L cell line showed a rightward shift in the profile when cells treated with vinblastine or taxol were assayed, but not when cells treated with etoposide was assayed, consistent with the results disclosed above. The MM double mutant cell line showed no flow cytometric profile shift in the presence of these drugs, but the profile was shifted rightward using UIC2 compared with MRK16 (compare FIGS. 6C and 6D). Vinblastine induced levels of UIC2 mAb reactivity in KK-L cells were roughly equivalent to binding levels seen with MM cells. MM cells showed high levels of UIC2 mAb binding in either the presence or absence of drugs (FIG. 6D); MRK16 binding was unaffected and observed at a level consistent with binding to KK-L cells, confirming our earlier observations on the relative Pgp expression levels of these cell lines.

In contrast with these results, the single mutant MK-H cells showed lower UIC2 reactivity than the wild-type KK-H transfectants, while the reactivity of the other single mutant cell line KM-H, was similar to KK-H (FIGS. 7A through 7F). The KK-H, MK-H and KM-H transfectants were all observed to yield increased UIC2 reactivity by Pgp substrates, with the final levels becoming very similar for all three cell lines (compare FIGS. 7A, 7C and 7E). MRK16 binding levels were approximately the same for all three cell lines in the presence or absence of drug.

These results demonstrated that enhanced UIC2 mAb binding was related to the conformation of Pgp expressed in UIC2-reactive cell lines, and suggested that the MM mutant had adopted a conformation equivalent to the biochemically active conformation presumed to be recognized by UIC2 and which accounted for enhanced UIC2 mAb binding to Pgp in the presence of certain Pgp substrates.

EXAMPLE 4

Intracellular ATP Depletion Maximized UIC2 Reactivity

Figure 8A:
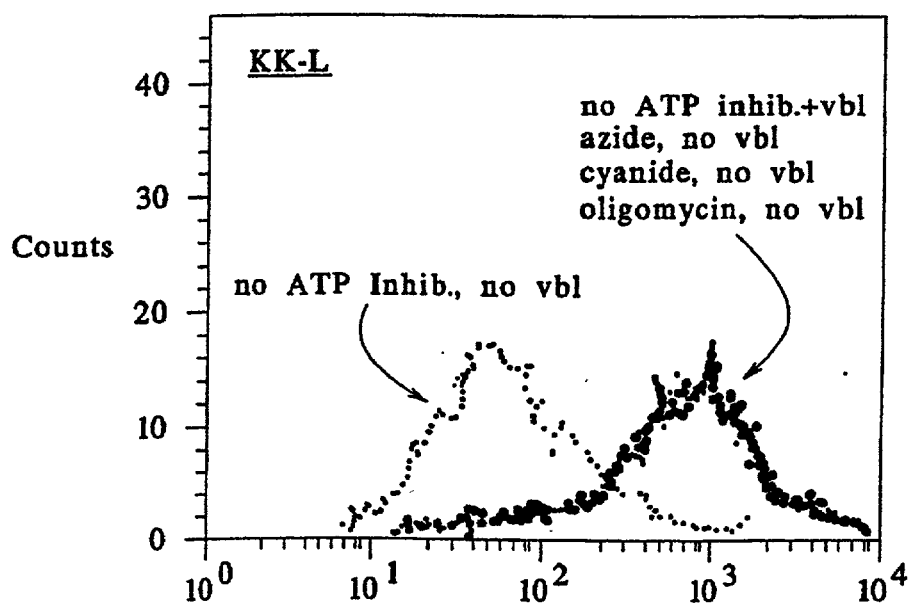
FIGS. 8A through 8E illustrate flow cytometric analysis of mouse L cell transfectants expressing wildtype (KK-L.
Figure 8B:
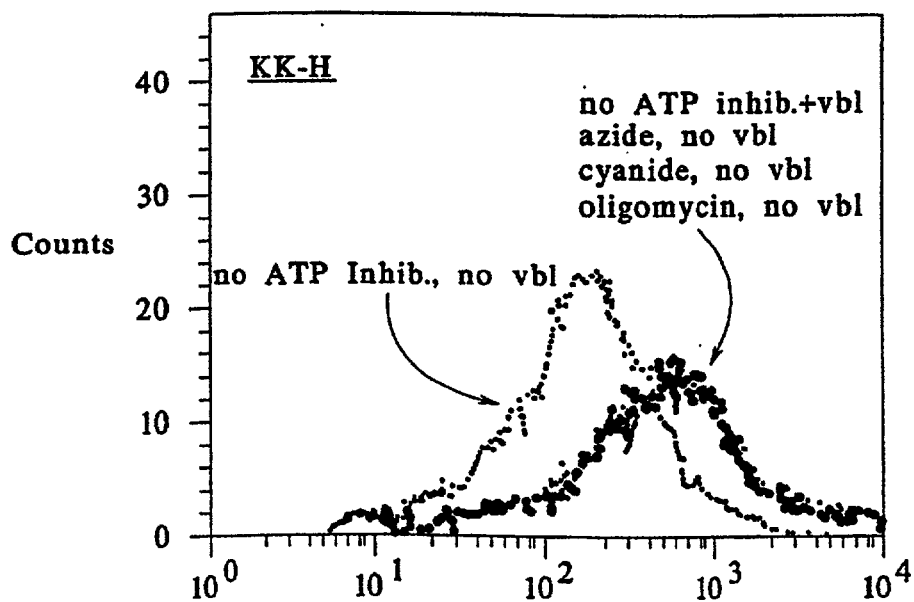
Figure 8C:
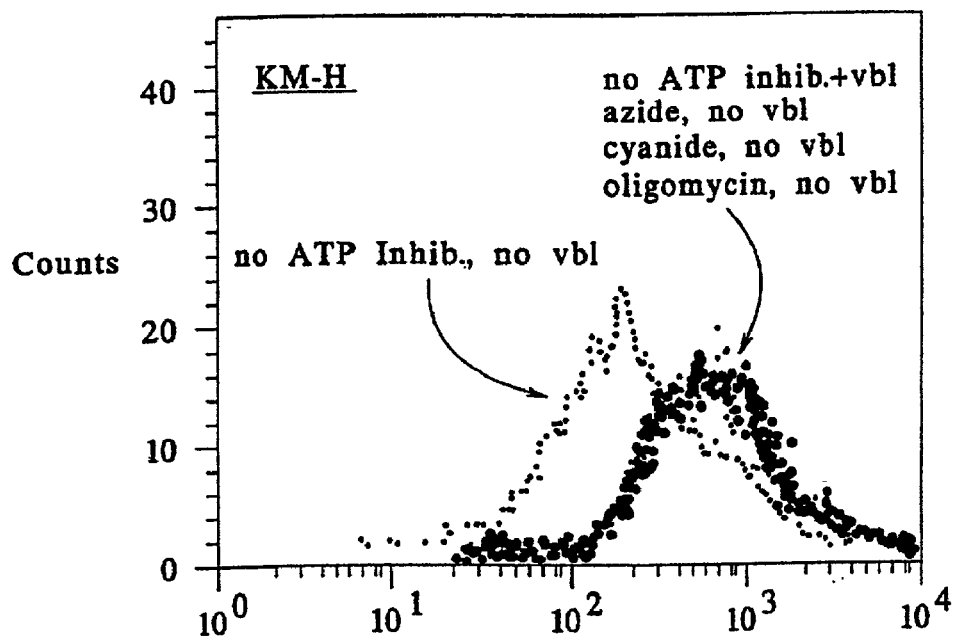
Figure 8D:
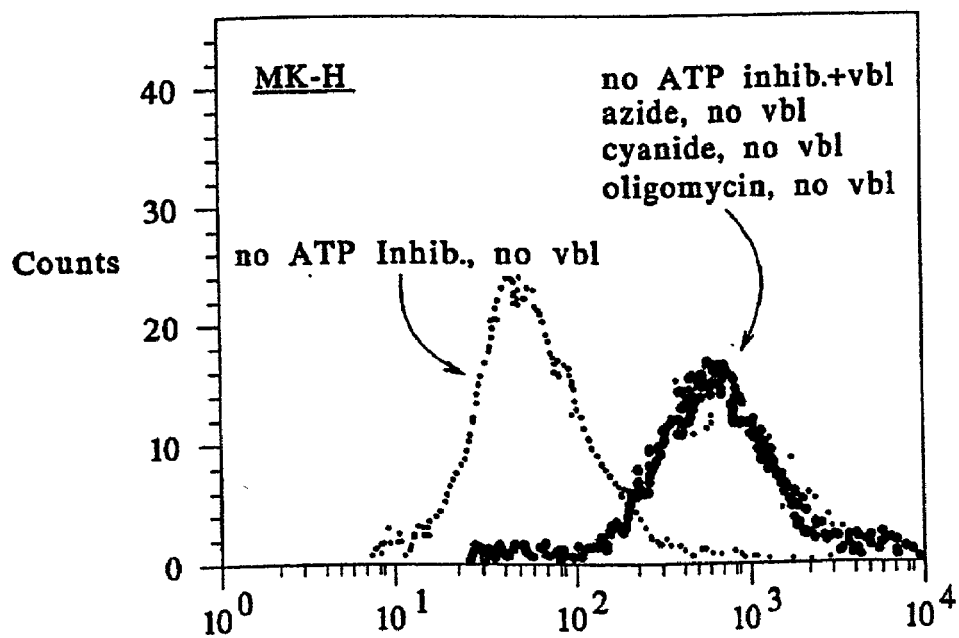
Figure 8E:
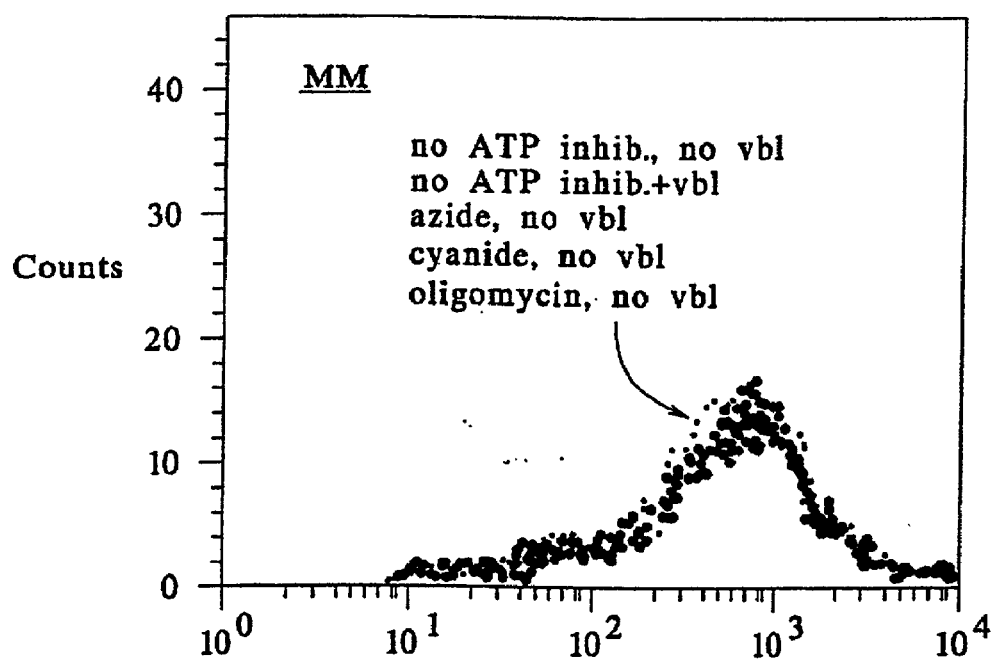
Figure 9A:
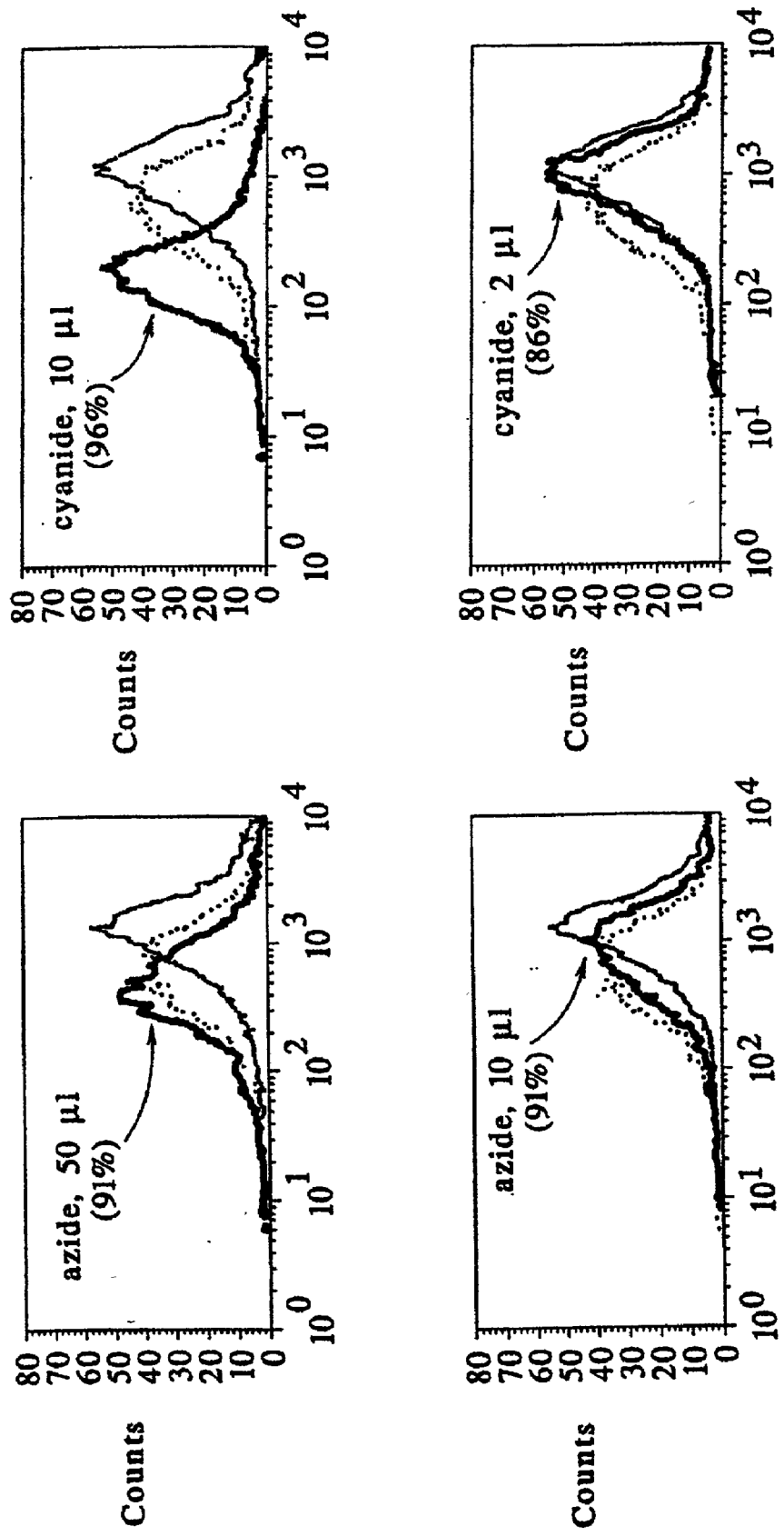
FIGS. 9A through 9C illustrate flow cytometric analysis of K562/i-S9 leukemia cells incubated with PE-conjugated UIC2 in the presence or absence of vinblastine and varying concentrations of the ATP depletion agents oligomycin, azide and cyanide.
Figure 9B:
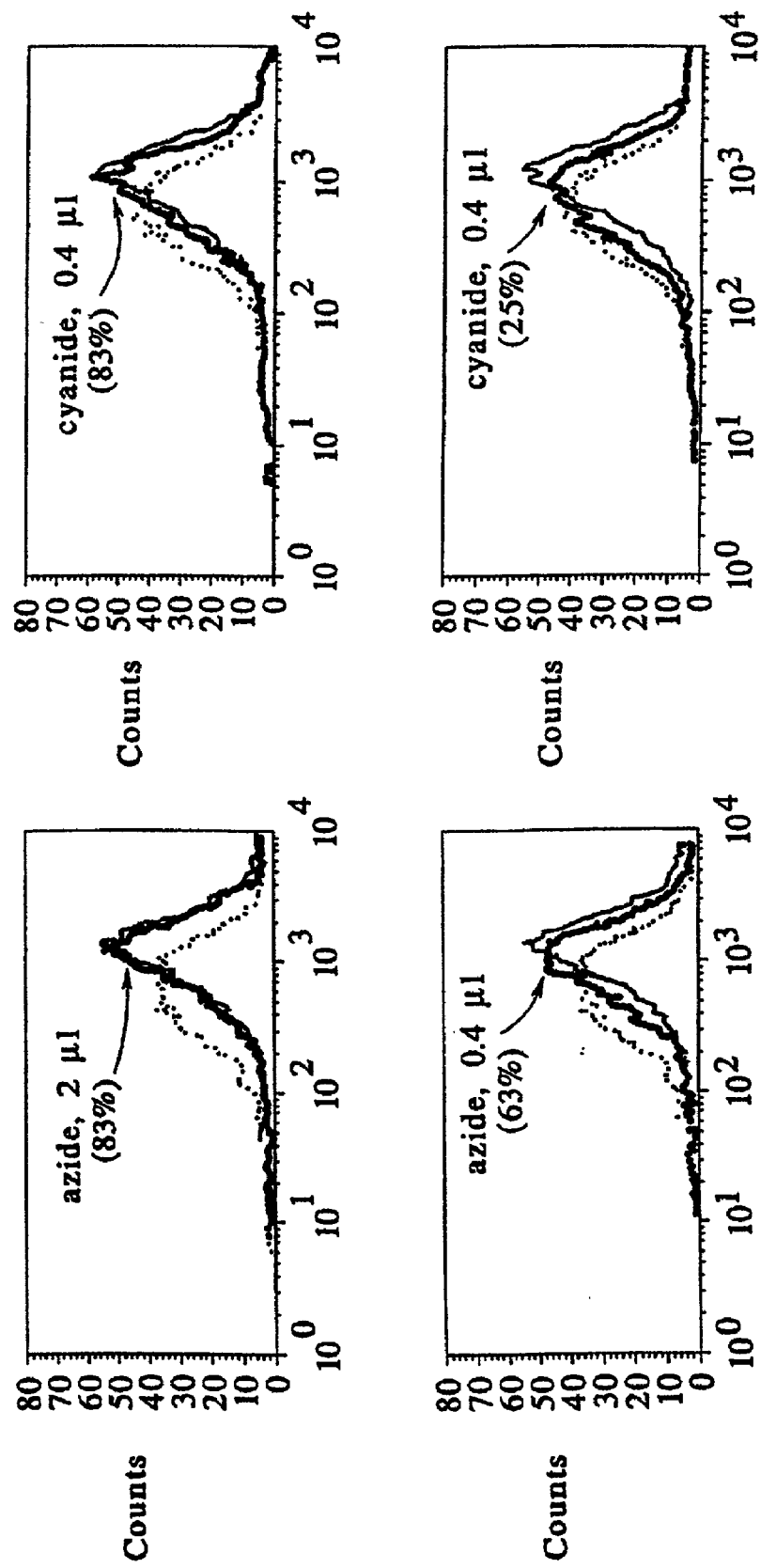
Figure 9C:
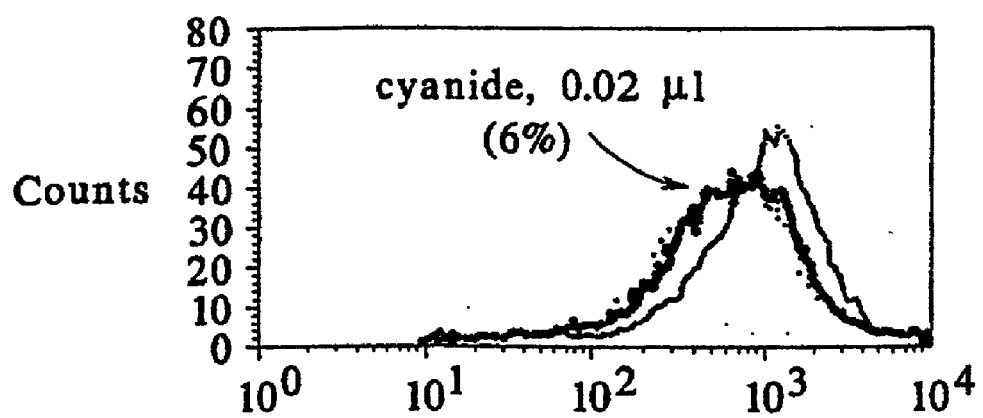

The results described in Example 3 above indicated that maximal UIC2 mAb reactivity was associated with the MM mutant, which carries disabling mutations in both nucleotide-binding sites. This result suggested that the biochemical conformation of Pgp that is specifically recognized by UIC2 mAb could reflect a conformation in which Pgp had no bound ATP. This further suggested that intracellular ATP depleting agents would increase UIC2 mAb reactivity for Pgp. Three different agents that induce ATP depletion, sodium cyanide, sodium azide and oligomycin (all of which are specific for mitochondrial enzymes and mechanisms which generate ATP) were used to deplete Pgp-expressing cells of intracellular ATP. All three agents were found to increase UIC2 mAb reactivity to wild-type Pgp in KK-L (FIG. 8A) and K562/I-S9 cells (FIGS. 9A through 9C); The increase in UIC2 reactivity correlated with the extent of intracellular ATP depletion, as measured by the luciferase assay described in Example 1.

Figure 10A:
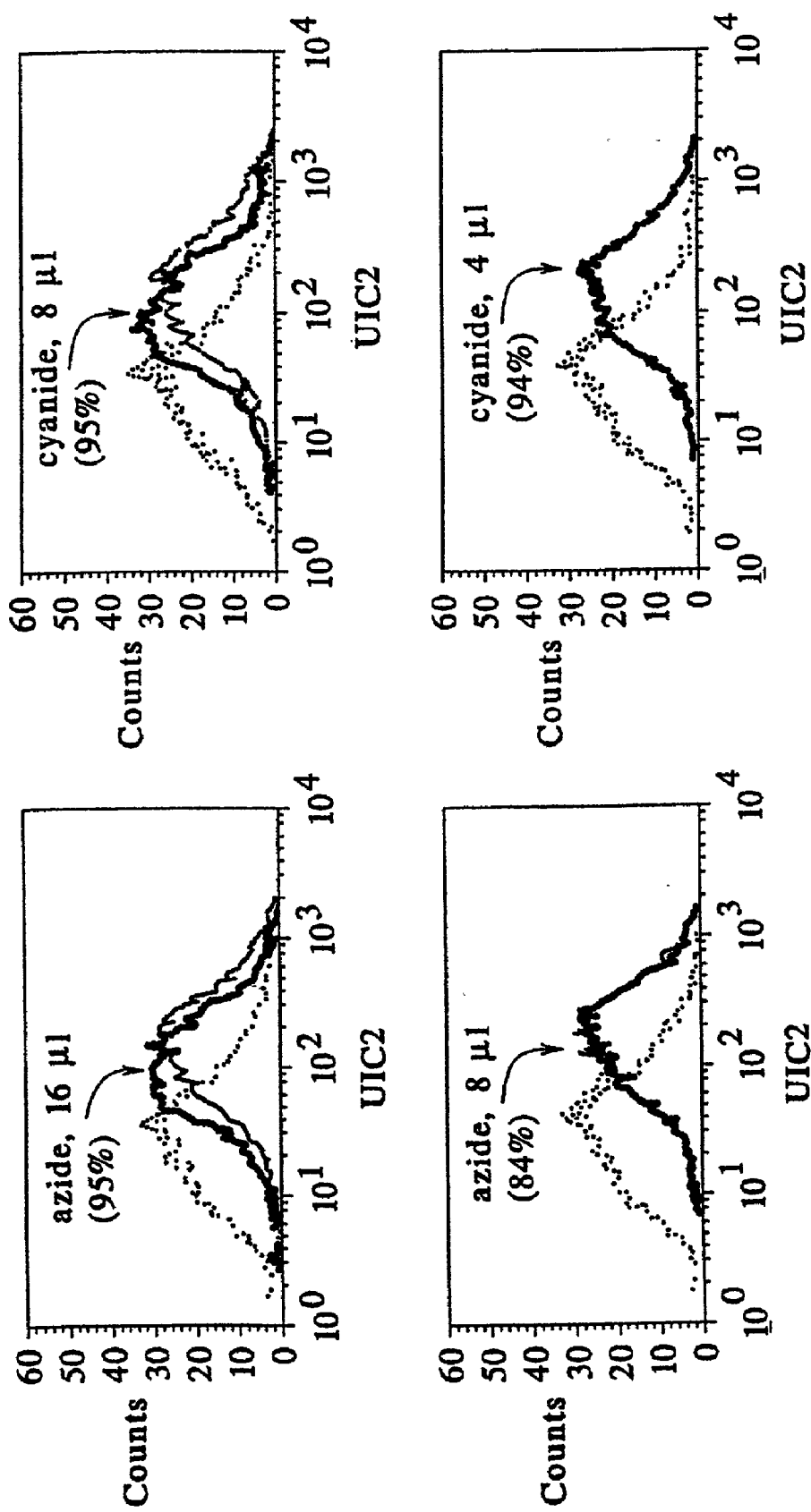
FIGS. 10A through 10D illustrate flow cytometric analysis of KK-L cells incubated with PE-conjugated UIC2 (FIGS. 10A and 10B) or MRK16 (FIGS. 10C and 10D) in the presence or absence of vinblastine and varying concentrations of the ATP depletion agents oligomycin, azide and cyanide.
Figure 10B:
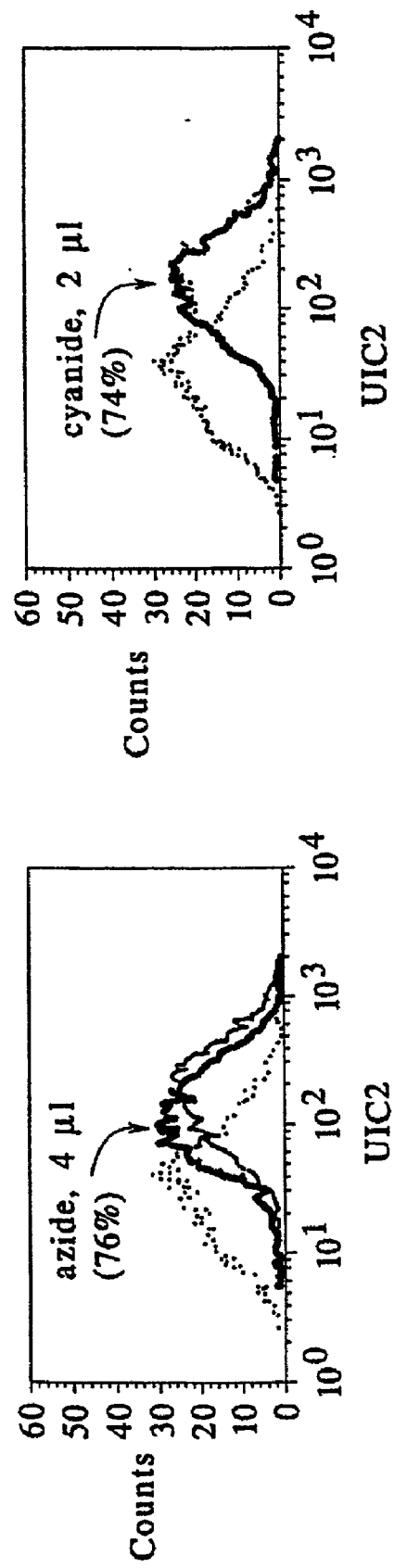
Figure 10C:
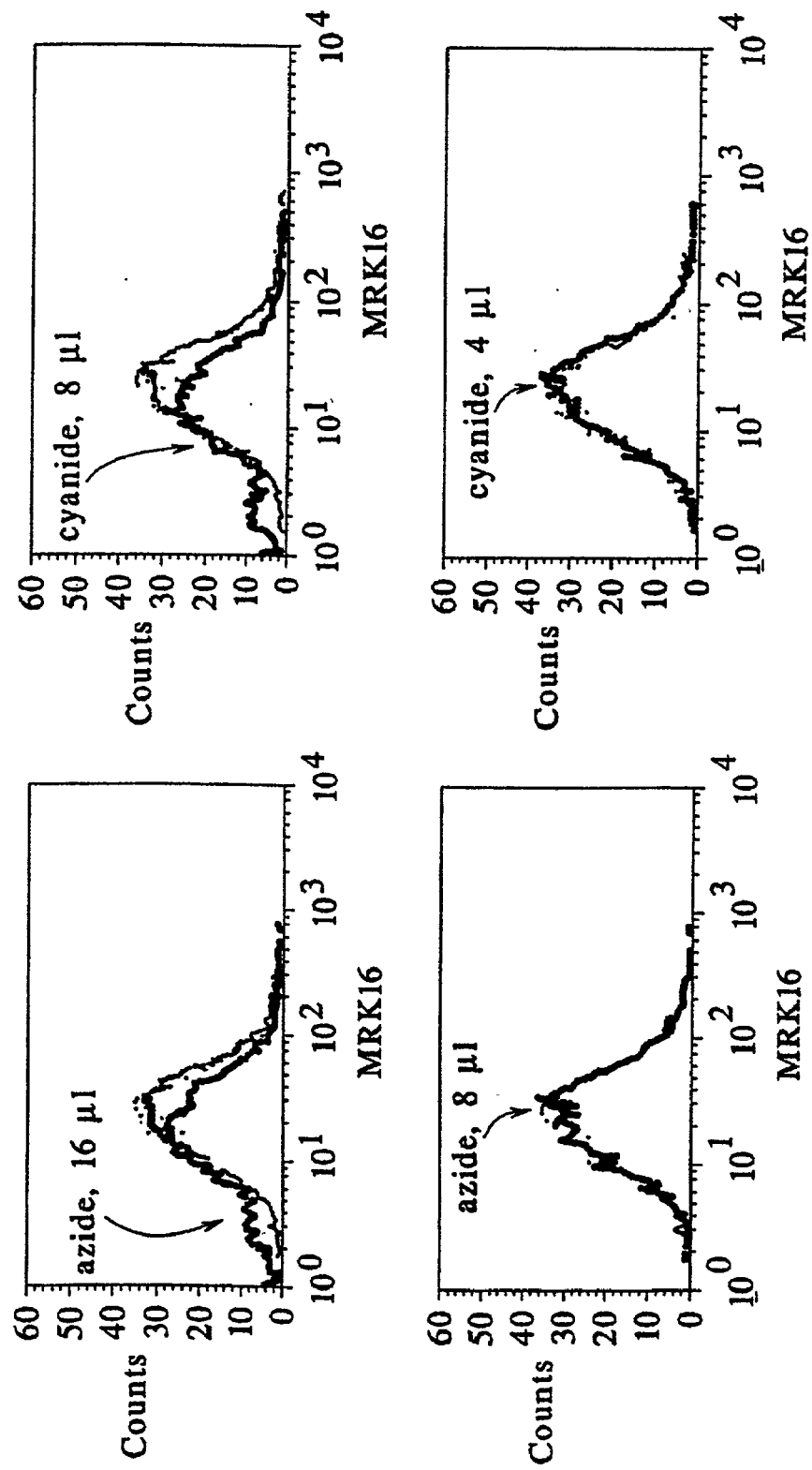
Figure 10D:
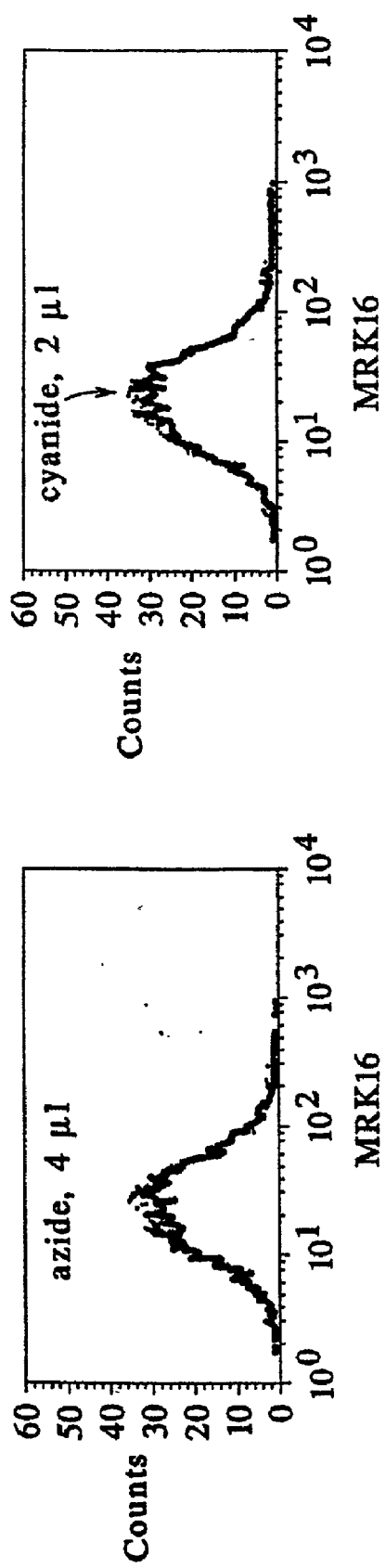

The addition of cyanide, azide or oligomycin to the series of LMtk⁻ cells transfected with different Pgp mutants had the same effect on UIC2 mAb reactivity as the addition of Pgp transport substrates (FIGS. 8A through 8E). These agents increased the reactivity of KK-L cells to the level of MM (compare FIGS. 8A and 8B), while having no effect on the MM cell reactivity, and increased the reactivity of KK-H, MK-H and KM-H cell lines to similar final levels. Similar results were obtained in K562/I-S9 cells expressing human Pgp (FIGS. 9A through 9C), and a comparison of UIC2 (FIG. 10A) and MRK16 (FIG. 10B) binding of KK-L cells expressing the wildtype human Pgp is shown in FIGS. 10A and 10B.

Thus, these results support the conclusion that ATP depleting agents have the same effect on UIC2 mAb reactivity as mutagenesis of both nucleotide-binding sites of Pgp.

EXAMPLE 5

Characterization of Pgp Binding of a Novel Anticancer Compound

A novel anticancer drug was tested using the UIC2 binding assay to determine whether it bound to Pgp.

SN-38 is the active species of CPT-11 (Irinothecan), a newly-developed drug for treating colon cancer. Several clinical trials have demonstrated the efficacy of CPT-11 in colon cancer patients. However, it was unclear if SN-38 is a Pgp-transported substrate. This is of particular importance in colon cancer because all colon cancer tumors express Pgp and, therefore, are intrinsically resistant to Pgp-transported cyctotoxic drugs.

Figure 11:
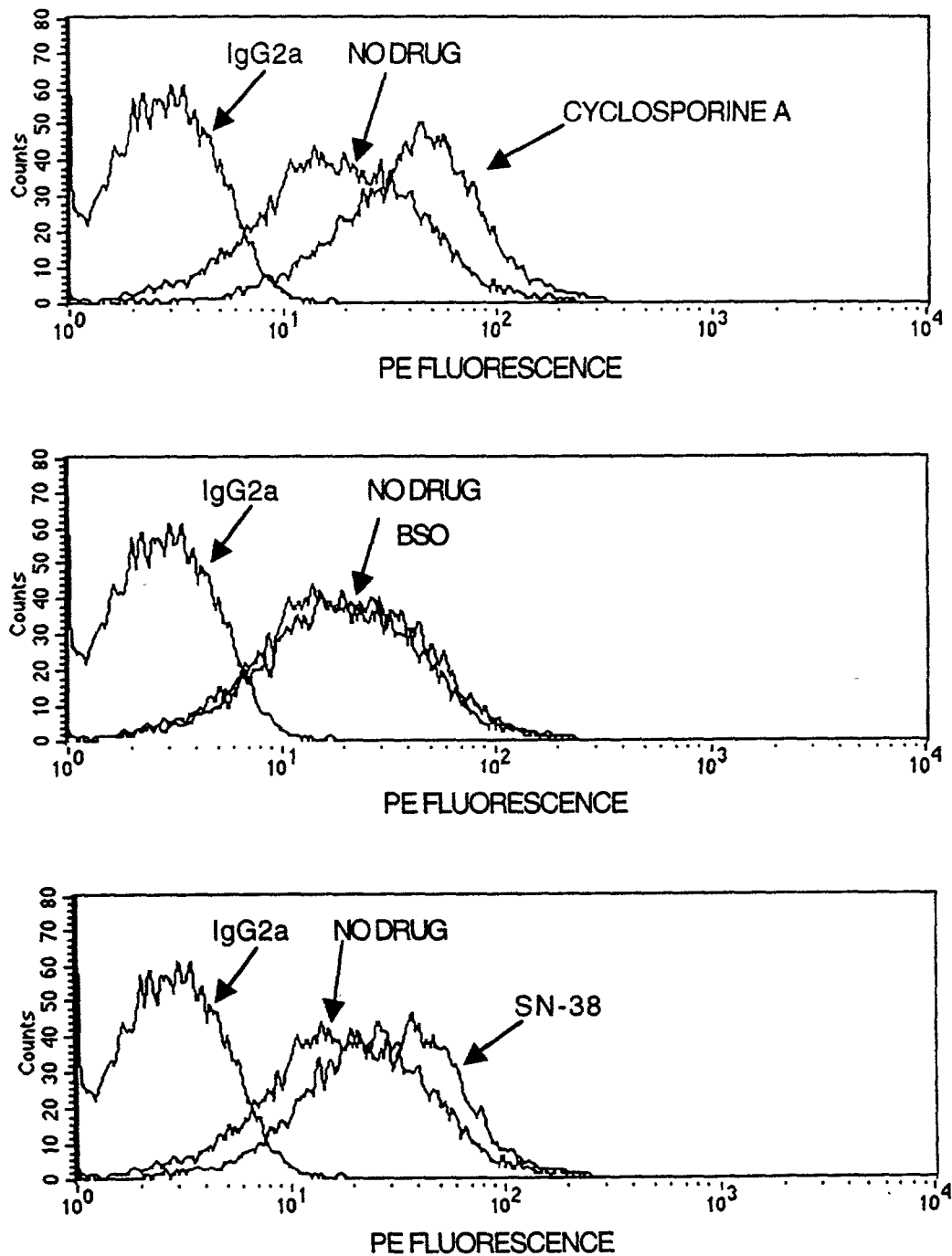
FIG. 11 illustrates flow cytometric analysis of K562/i-S9 leukemia cells incubated with PE-conjugated UIC2 in the presence or absence of cyclosporine, BSO or SN-38 as described in Example 5.

A modification of the UIC2 binding assay was used to determine Pgp substrate specificity of SN-38 in vitro. Flow cytometry was performed on the K562/S9-I cell line, which had been infected with a retrovirus containing human MDR1 cDNA and selected for Pgp expression by flow sorting. Washed K562/S9-I cells were incubated in phosphate-buffered solution (PBS) with 2% FCS for 10 min at 37° C. in the presence of SN-38, cyclosporin-A (a known Pgp substrate as a positive control) or buthionine sulfoximine (BSO, a non-Pgp drug as a negative control for UIC2 shift) at the final concentration of 5 mg/mL. The cells were then incubated with UIC2 labeled with phycoerythrin (UIC2-PE, obtained from Immunotech, Marseille, France), or IgG2a-PE (an mAb isotype control) for 20 minutes at 37° C. in the presence of the above drugs. The treated samples were washed twice with cold PBS, mixed with propodium iodide (to exclude non-viable cells) and analyzed using the BDIS FACSVantage cell sorter. A DMSO control was also used in the experiment to exclude the possibility that this diluent affects UIC2 staining. As shown in FIG. 11, cyclosporine A induced UIC2 shift (increased immunoreactivity, as compared to "no drug" DMSO control), while treatment with BSO, a non-Pgp drug, did not result n UIC2 shift in K562/S9-I cells. Incubation of K562/S9-I cells with UIC2-PE in the presence of SN-38 under physiological conditions induced UIC2 shift, demonstrating that this drug is a Pgp-transported substrate.

This result was confirmed in additional experiments performed using a Pgp-positive breast cancer cell line, MCF7-P4 Pgp-positive breast carcinoma cell line; in these assays, cisplatin was used as a negative control. These results are shown in FIG. 12, wherein binding of labeled UIC2 to these cells was enhanced in the presence of SN-38.

There results established that SN-38 is a Pgp-biding drug. These results have been confirmed by conventional in vitro cytotoxicity tests.

EXAMPLE 6

Characterization of Pgp Binding of a Novel Anticancer Compound

The cytotxic drugs taxol and taxotere are commonly-used chemotherapeutic agents for treating a variety of human cancers, including breast, lung and ovarian tumors, as well as Kaposi's sarcoma. Taxol was initially purified from Pacific yew tree bark, and currently its semi-synthetic form is manufactured from other renewable sources. Taxotere is a semi-synthetic compound derived from the needles of European yew tree. Both drugs are very similar with respect to their chemical structure and mechanism of cytotoxic action on microtubules in tumor cells.

Figure 13:
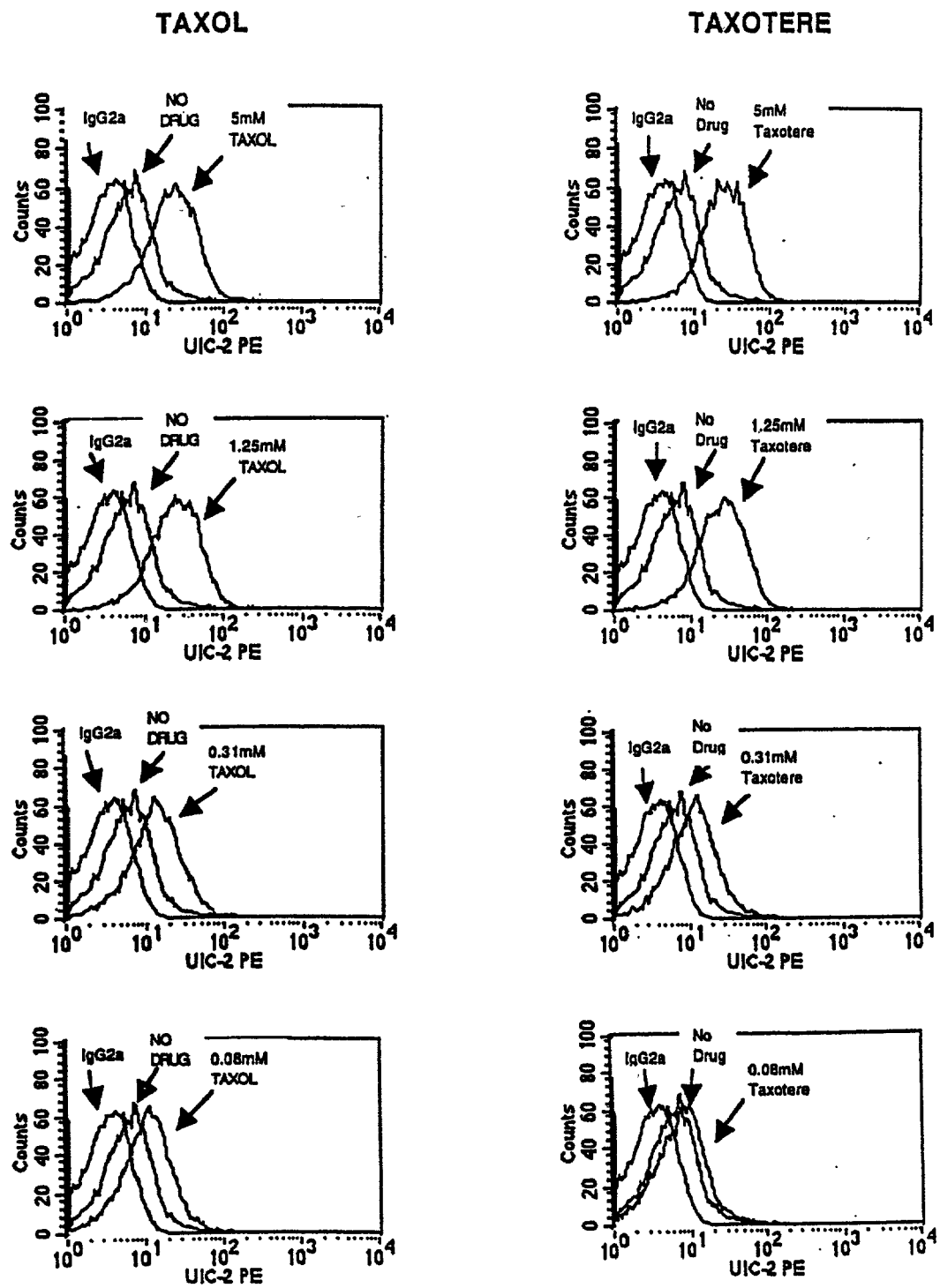
FIG. 13 illustrates flow cytometric analysis of human KB-8-5 tumor cells incubated with PE-conjugated UIC2 in the presence or absence of taxol or taxotere as described in Example 6.

It has been previously shown that both taxol and taxotere can be effluxed by the Pgp pump in human tumors. However, it had also been shown that taxotere had higher anticancer efficacy than taxol in clinical trials on breast and ovarian tumors. One explanation for the clinical data was that this difference in the drugs' activity was caused by their differences in their Pgp substrate specificity. The modification of the UIC2 binding assay described in Example 5 was used to determine relative Pgp transport specificities for taxol and taxotere. In these experiments, a human tumor cell line, KB-8-5, was incubated as described above with PE-labeled UIC2 in the presence of taxol or taxotere at four concentrations: 0.08 mM, 0.31 mM, 1.25 mM, and 5 mM, using DMSO diluent alone as a negative substrate control and mouse IgG2a as a negative mAb control. Flow cytometric analysis was performed as described, and the results are shown in FIG. 13. At low concentrations (0.08 mM and 0.31 mM), taxotere was found to induce a smaller binding affinity shift than taxol at equivalent concentrations (compare the two cytometric analysis curves on the lower left with the two on the lower right in FIG. 13). These results were not as evidence in the analyses performed at higher drug concentrations. These observation indicated that the taxotere is effuxed less efficiently from these cells than taxol, leading to increased intracellular taxotere accumulation and the higher therapeutic efficiency found clinically in cancer patients. This finding was confirmed by conventional in vitro cytotoxicity experiments demonstrating that intracellular accumulation of taxotere is higher than that of taxol These results demonstrate that the methods of the invention can be used to characterize and compare novel anticancer drugs for Pgp binding efficiency, and that these results can be used to identify anticancer compounds having higher clinical efficacy based on lower affinity for Pgp.

It should be understood that the foregoing disclosure emphasizes certain specific embodiments of the invention and that all modifications or alternatives equivalent thereto are within the spirit and scope of the invention as set forth in the appended claims.

We claim:

1. A method for screening a compound for P-glycoprotein binding comprising the steps of
   a. incubating a mammalian cell expressing P-glycoprotein in the presence or absence of a compound.
   b. reacting the mammalian cell with an immunological reagent specific for P-glycoprotein in a biochemical conformation adopted In the presence of a P-glycoprotein substrate; and
   c comparing binding of the immunological reagent to the cell in the presence of the compound with binding in the absence of the compound.

2. The method of claim 1 wherein the immunological reagent is a monoclonal antibody specific for P-glycoprotein in a biochemical conformation adopted in the presence of a P-glycoprotein substrate.

3. The method of claim 1 wherein binding of the immunological reagent is increased in the presence of P-glycoprotein substrate.

4. The method of claim 1 wherein the immunological reagent is detectably-labeled.

5. The method of claim 4 wherein the detectable label is a fluorescence label.

6. The method of claim 5 wherein the reagent is detected by fluorescence-activated cell sorting.

* * * * *